US010300042B2

(12) United States Patent
Hough et al.

(10) Patent No.: US 10,300,042 B2
(45) Date of Patent: May 28, 2019

(54) APREMILAST FOR THE TREATMENT OF A LIVER DISEASE OR A LIVER FUNCTION ABNORMALITY

(71) Applicant: Celgene Corporation, Summit, NJ (US)

(72) Inventors: Douglas Hough, Martinsville, NJ (US); Randall Stevens, Rockport, MA (US)

(73) Assignee: Celgene Corporation, Summit, NJ (US)

( * ) Notice: Subject to any disclaimer, the term of this patent is extended or adjusted under 35 U.S.C. 154(b) by 68 days.

(21) Appl. No.: 15/321,718

(22) PCT Filed: Jun. 22, 2015

(86) PCT No.: PCT/US2015/036898
§ 371 (c)(1),
(2) Date: Dec. 22, 2016

(87) PCT Pub. No.: WO2015/200177
PCT Pub. Date: Dec. 30, 2015

(65) Prior Publication Data
US 2017/0143671 A1 May 25, 2017

Related U.S. Application Data

(60) Provisional application No. 62/016,013, filed on Jun. 23, 2014.

(51) Int. Cl.
*A61K 31/4035* (2006.01)

(52) U.S. Cl.
CPC .................................. *A61K 31/4035* (2013.01)

(58) Field of Classification Search
CPC .................................................. A61K 31/4035
See application file for complete search history.

(56) References Cited

U.S. PATENT DOCUMENTS

| | | |
|---|---|---|
| 3,031,450 A | 4/1962 | Fischer et al. |
| 3,322,755 A | 5/1967 | Roch et al. |
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 3,920,636 A | 11/1975 | Takahashi et al. |
| 4,001,237 A | 1/1977 | Partyka et al. |
| 4,001,238 A | 1/1977 | Partyka et al. |
| 4,008,719 A | 2/1977 | Theeuwes et al. |
| 4,047,404 A | 9/1977 | Hayashi |
| 4,060,615 A | 11/1977 | Matier et al. |
| 4,101,548 A | 7/1978 | Crenshaw et al. |
| 4,162,316 A | 7/1979 | Nishimura et al. |
| 4,209,623 A | 6/1980 | Juby |
| 4,880,810 A | 11/1989 | Lowe, III |
| 4,885,301 A | 12/1989 | Coates |
| 5,059,595 A | 10/1991 | Le Grazie |
| 5,073,543 A | 12/1991 | Marshall et al. |
| 5,120,548 A | 6/1992 | McClelland et al. |
| 5,147,875 A | 9/1992 | Coates et al. |
| 5,354,556 A | 10/1994 | Sparks et al. |
| 5,354,571 A | 10/1994 | Morikawa et al. |
| 5,401,774 A | 3/1995 | Pamukcu et al. |
| 5,439,895 A | 8/1995 | Lee et al. |
| 5,488,055 A | 1/1996 | Kumar et al. |
| 5,591,767 A | 1/1997 | Mohr et al. |
| 5,608,914 A | 3/1997 | Keesler |
| 5,614,530 A | 3/1997 | Kumar et al. |
| 5,614,627 A | 3/1997 | Takase et al. |
| 5,639,476 A | 6/1997 | Oshlack et al. |
| 5,658,940 A | 8/1997 | Muller et al. |
| 5,674,533 A | 10/1997 | Santus et al. |
| 5,698,579 A | 12/1997 | Muller |
| 5,703,098 A | 12/1997 | Muller et al. |
| 5,710,170 A | 1/1998 | Guay et al. |
| 5,728,844 A | 3/1998 | Muller et al. |
| 5,728,845 A | 3/1998 | Muller et al. |
| 5,733,566 A | 3/1998 | Lewis |
| 5,736,570 A | 4/1998 | Muller et al. |
| 5,798,373 A | 8/1998 | Warrellow |
| 5,801,195 A | 9/1998 | Muller et al. |
| 5,849,770 A | 12/1998 | Head et al. |
| 5,877,200 A | 3/1999 | Muller |
| 5,891,896 A | 4/1999 | Warrellow et al. |
| 6,011,050 A | 1/2000 | Muller et al. |
| 6,020,339 A | 2/2000 | Perrier et al. |
| 6,020,358 A | 2/2000 | Muller et al. |
| 6,034,089 A | 3/2000 | Han et al. |

(Continued)

FOREIGN PATENT DOCUMENTS

| | | |
|---|---|---|
| CN | 104761484 A | 7/2015 |
| DE | 2051871 A1 | 11/1971 |

(Continued)

OTHER PUBLICATIONS

Vippagunta, et al. Advanced Drug Delivery Reviews 48 (2001) 3-26.* U.S. Appl. No. 60/454,155, filed Mar. 12, 2003, Muller et al.
U.S. Appl. No. 60/454,149, filed Mar. 12, 2003, Muller et al.
U.S. Appl. No. 60/438,448, filed Jan. 7, 2003, Schafer et al.
U.S. Appl. No. 60/438,450, filed Jan. 7, 2003, Muller et al.
U.S. Appl. No. 60/436,975, filed Dec. 30, 2002, Muller et al.
U.S. Appl. No. 60/366,515, filed Mar. 20, 2002, Muller et al.
Akazome, M. et al., "Asymmetric recognition of 1-arylethylamines by (R)-phenylglycyl-(R)-phenylglycine and its mechanism," Tetrahedron: Asymmetry, Elsevier Science Publishers, Amsterdam, NL, 8(14):2331-2336 (1997).
Akoğlu et al., "TNF, soluble IL-2R and soluble CD-8 in Behçet's disease," Journal of Rheumataology, 17(8):1107-1108 (1990).

(Continued)

*Primary Examiner* — Shawquia Jackson
(74) *Attorney, Agent, or Firm* — Jones Day

(57) ABSTRACT

Methods of treating, managing or preventing liver disease are disclosed. Specific methods encompass the administration of apremilast, alone or in combination with additional active agents or treatment regimens.

34 Claims, No Drawings

(56) References Cited

U.S. PATENT DOCUMENTS

| | | | |
|---|---|---|---|
| 6,046,221 | A | 4/2000 | Muller et al. |
| 6,069,156 | A | 5/2000 | Oku et al. |
| 6,162,830 | A | 12/2000 | Connor et al. |
| 6,166,041 | A | 12/2000 | Cavalla et al. |
| 6,177,471 | B1 | 1/2001 | Menander et al. |
| 6,204,275 | B1 | 3/2001 | Friesen et al. |
| 6,218,400 | B1 | 4/2001 | Daugan et al. |
| 6,300,335 | B1 | 10/2001 | Campbell et al. |
| 6,316,472 | B1 | 11/2001 | Frenette et al. |
| 6,333,354 | B1 | 12/2001 | Schudt |
| 6,962,940 | B2 | 11/2005 | Muller et al. |
| 7,208,516 | B2 | 4/2007 | Muller et al. |
| 7,276,529 | B2 | 10/2007 | Muller et al. |
| 7,358,272 | B2 | 4/2008 | Muller et al. |
| 7,427,638 | B2 | 9/2008 | Muller et al. |
| 7,507,759 | B2 | 3/2009 | Muller et al. |
| 7,659,302 | B2 | 2/2010 | Muller et al. |
| 7,659,303 | B2 | 2/2010 | Muller et al. |
| 7,799,782 | B2 | 9/2010 | Munson et al. |
| 7,893,101 | B2 | 2/2011 | Muller et al. |
| 8,093,283 | B2 | 1/2012 | Muller et al. |
| 8,455,536 | B2 | 6/2013 | Muller et al. |
| 8,629,173 | B2 | 1/2014 | Muller et al. |
| 8,802,717 | B2 | 8/2014 | Muller et al. |
| 9,018,243 | B2 | 4/2015 | Muller et al. |
| 9,283,207 | B2 | 3/2016 | Muller et al. |
| 9,724,330 | B2 | 8/2017 | Muller et al. |
| 2008/0027123 | A1 | 1/2008 | Muller et al. |
| 2008/0234359 | A1* | 9/2008 | Muller et al. |
| 2010/0324108 | A1 | 12/2010 | Liu |

FOREIGN PATENT DOCUMENTS

| | | |
|---|---|---|
| EP | 0 347 146 | 6/1989 |
| EP | 0 349 239 | 6/1989 |
| EP | 0 351 058 | 6/1989 |
| EP | 0 352 960 | 7/1989 |
| EP | 0 395 328 | 4/1990 |
| EP | 0 428 268 | 10/1990 |
| EP | 0 463 756 | 6/1991 |
| EP | 0 526 004 | 7/1992 |
| EP | 0 607 439 | 9/1992 |
| EP | 0 722 937 | 1/1996 |
| EP | 0 722 943 | 1/1996 |
| EP | 0 722 944 | 1/1996 |
| EP | 1752148 B1 | 6/2010 |
| GB | 2 063 249 | 9/1980 |
| WO | WO 93/07149 | 4/1993 |
| WO | WO 93/12095 | 6/1993 |
| WO | WO 94/01728 | 1/1994 |
| WO | WO 94/05661 | 3/1994 |
| WO | WO 94/29277 | 12/1994 |
| WO | WO 95/19978 | 7/1995 |
| WO | WO 96/32379 | 10/1996 |
| WO | WO 97/03070 | 1/1997 |
| WO | WO 97/03675 | 2/1997 |
| WO | WO 97/03985 | 2/1997 |
| WO | WO 97/24334 | 7/1997 |
| WO | WO 98/06722 | 2/1998 |
| WO | WO 98/08848 | 3/1998 |
| WO | WO 98/14448 | 4/1998 |
| WO | WO 98/16521 | 4/1998 |
| WO | WO 98/17668 | 4/1998 |
| WO | WO 98/23597 | 6/1998 |
| WO | WO 98/38168 | 9/1998 |
| WO | WO 99/06041 | 2/1999 |
| WO | WO 00/25777 | 5/2000 |
| WO | WO 01/34606 | 5/2001 |
| WO | WO 01/47915 | 7/2001 |
| WO | WO 03/080049 | 10/2003 |
| WO | WO 2009/120167 | 10/2009 |
| WO | WO 2010/030345 | 3/2010 |
| WO | WO 2011/063102 | 5/2011 |

OTHER PUBLICATIONS

Bond et al., Controlling Crystal Architecture in Molecular Solids: The Supramolecular Approach, In Supramolecular Organization and Materials Design, 391, 436 (W. Jones & C. N. R. Rao, eds., 2002).

Au et al., "Effect of PDE4 inhibitors on zymosan-induced IL-8 release from human neutrophils: synergism with prostanoids and salbutamol," Brit. J. Pharm. 123:1260-1266 (1998).

Baehr et al., "Isolation and characterization of cGMP phosphodiesterase from bovine rod outer segments," J. Biol. Chem. 254:11669-11677 (1979).

Balasubramanian et al., "Synthesis of β-amino-sulphones and up-unsaturated sulphones, Part II," J. Chem. Soc., 3296-3298 (1955).

Banker et al., "Modern Pharmaceutics," $4^{th}$ edition, Marcel Dekker, Inc., New York, New York, 172-174 (2002).

Baughman et al., "Release of tumor necrosis factor by alveolar macrophages of patients with sarcoidosis," J. Lab. Clin. Med. 115:36-42 (1990).

Bavin, "Process Development—Polymorphism in process development," Chemistry & Industry, 527-529 (1989).

Beavo and Reifsnyder, "Primary sequence of cyclic nucleotide phosphodiesterase isozymes and the design of selective inhibitors," Trends in Pharm., 11:150-155 (1990).

Berge et al., "Pharmaceutical Salts," Journal of Pharmaceutical Sciences, 66(1):1-19 (1977).

Bernstein, "Polymorphism in molecular crystals," Clarendon Press, Oxford, 6 pages (2002).

Bertolini et al., "Stimulation of bone resorption and inhibition of bone formation in vitro by human tumour necrosis factors," Nature, 319(6053)516-518 (1986).

Bissonnette et al., "Pulmonary inflammation and fibrosis in a murine model of asbestosis and silicosis. Possible role of tumor necrosis factor," Inflammation 13:329-339 (1989).

Bloom et al., "Identification and tissue-specific expression of PDE7 phosphodiesterase splice variants," Proc. Natl. Acad. Sci. USA 93:14188-14192 (1996).

Brackeen et al., "Design and Synthesis of Conformationally Constrained Analogues of 4-(3-Butoxy-4-Methoxybenzyl) Imidazolidin-2-one (Ro 20/1724) as Potent Inhibitors of cAMP-Specific Phosphodiesterase", J. Med. Chem. 38:4848-4854 (1995).

Brittain et al., "Effects of pharmaceutical processing on drug polymorphs and solvates," in Polymorphism Pharmaceutical Solids, Marcel Dekker, Inc., New York, New York, 331-361 (1999).

Bundgaard, Hans, "Design of Prodrugs: Bioreversible Derivatives for Various Functional Groups and Chemical Entities," Design of Prodrugs, Chapter 1: 1-4 (1985).

Byrn et al., "Pharmaceutical solids: a strategic approach to regulatory considerations," Pharmaceutical Research, 12(7):945-954 (1995).

Caira, "Crystalline polymorphism of organic compounds," *Top. Curr. Chem.*, 198:163-208 (1998).

Carstensen, Drug Stability: Principles & Practice, 2nd ed., Marcel Dekker, New York, NY pp. 379-80 (1995).

Casini et al., "Preparation of One of the Optical Antipodes of 2-Phthalimidoglutarimide," Farmaco Ed. Sci. 19:563-565 (1964).

Celgene press release, "Apremilast ESTEEM program meets primary and major secondary endpoint in pivotal phase III psoriasis trials," dated Jan. 7, 2013.

Celgene press release, "Positive phase IIB topline clinical data for Celgene oral compound apremilast (CC-10004) reported for patients with moderate-to-severe psoriasis," Dec. 15, 2009.

Chae et al., "Pentoxifylline attenuates methionine- and choline-deficient-diet-induced steatohepatitis by suppressing TNF-α expression and endoplasmic reticulum stress," *Exp. Diabetes Res.*, 2012:762565 (2012).

Chemburkar et al., "Dealing with the impact of ritonavir polymorphs on the late stages of bulk drug process development," Org. Process Res. Dev., 4:413-417 (2000).

Chemistry in Britain ,"Side-effects kill new prozac," p. 11 (2000).

Clouse et al., "Monokine regulation of human immunodeficiency virus-1 expression in a chronically infected human T cell clone," J. Immunol. 142:431-438 (1989).

(56) References Cited

OTHER PUBLICATIONS

Corral et al., "Selection of novel analogs of thalidomide with enhanced tumor necrosis factor α inhibitory activity," Mol. Med., 2(4):506-515 (1996).
Craven et al., CAS: 71-117431 (1969).
Decision of the Appeal Board with Minutes of the Oral Proceedings, Mar. 17, 2015, in Opposition to EP Patent No. 1485087.
Decision to Grant EP Application No. 08742326.5, dated Apr. 10, 2014.
Decision with Minutes of the Oral Proceedings, dated May 19, 2011, in Opposition of EP Patent No. 1485087.
Declaration of Professor William Jones, Ph.D., dated Sep. 11, 2015.
Derian et al., "Inhibition of chemotactic peptide-induced neutrophil adhesion to vascular endothelium by cAMP modulators," J. Immunol. 154:308-317 (1995).
Dezube et al., "Pentoxifylline and wellbeing in patients with cancer," Lancet, 335:662 (1990).
Dredge et al., "Angiogenesis Inhibitors in Cancer Therapy," Curr. Opin. Investig. Drugs 4(6):667-674 (2003).
Dredge et al., "Immunological effects of thalidomide and its chemical and functional analogs," Crit. Rev. Immunol. 22(5-6):425-437 (2002).
Dredge et al., "Recent Developments in Antiangiogenic Therapy," Expert Opin. Biol. Ther. 2(8):953-966 (2002).
Duh et al., "Tumor necrosis factor alpha activates human immunodeficiency virus type 1 through induction of nuclear factor binding to the NF-kappa B sites in the long terminal repeat," Proc. Nat. Acad. Sci. 86:5974-5978 (1989).
Elliott et al., "TNFα Blockade in rheumatoid arthritis: rationale, clinical outcomes and mechanisms of action," Int. J. Immunopharmac., 17(2):141-145 (1995).
European Commission's Decision to grant Marketing Authorization for Otezla, dated Jan. 15, 2015.
Experimental Report (Ham), Lek Pharmaceuticals, Jan. 29, 2015.
Experimental Report (Kórodi) dated Feb. 5, 2015.
Experimental Report, submitted in Opposition proceedings for EP Patent No. 2276483, dated Feb. 6, 2015.
Featherstone et al., "Comparison of Phosphodiesterase Inhibitors of Differing Isoenzyme Selectivity Added to St. Thomas' Hospital Cardioplegic Solution Used for Hypothermic Preservation of Rat Lungs", Am. J. Respir. Crit. Care Med. 162:850-856 (2000).
Ferrai-Baliviera et al., "Tumor necrosis factor induces adult respiratory distress syndrome in rats," Arch. Surg., 124(12):1400-1405 (1989).
Folks et al., "Tumor necrosis factor alpha induces expression of human immunodeficiency virus in a chronically infected T-cell clone," Proc. Natl. Acad. Sci., USA, 86(7):2365-2368 (1989).
Furniss et al., "Vogel's Textbook of Practical Organic Chemistry," 5th edition, John Wiley & Sons, Inc., New York, New York, 134-143 (1989).
Gee et al., "Selective Cytokine Inhibitory Drugs With Enhanced Antiangiogenic Activity Control Tumor Growth Through Vascular Inhibition," Cancer Res. 63(23):8073-8078 (2003).
Gillespie et al., "Inhibition and stimulation of photoreceptor phosphodiesterases by dipyridamole and M&B 22,948," Mol. Pharm. 36:773-781 (1989).
Gottlieb et al., "An open-label, single-arm pilot study in patients with severe plaque-type psoriasis treated with an oral anti-inflammatory agent, apremilast," Current Medical Research and Opinion, 24(5):1529-1538 (2008).
Grant, "Theory and origin of polymorphosim," in *Polymoprhis in Pharmaceuticals Solids*, Ed. H. G. Brittain, Marcel Dekker, Inc., New York, NY, pp. 1-33 (1999).
Grau et al., "Tumor necrosis factor and disease severity in children with falciparum malaria," N. Engl. J. Med., 320(24):1586-1591 (1989).
Guillory, "Generation of polymophs, hydrates, solvates, and amorphous solids," in *Polymoprhis in Pharmaceuticals Solids*, Ed. H. G. Brittain, Marcel Dekker, Inc., New York, NY, pp. 183-226 (1999).

Hatzelmann and Schudt, "Anti-inflammatory and immunomodulatory potential of the novel PDE4 inhbitor roflumilast in vitro," J. Pharm. Exper. Ther., 297(1):267-279 (2001).
Hidaka and Asano, "Human blood platelet 3': 5'-cyclic nucleotide phosphodiesterase. Isolation of low-Km and high-Km phosphodiesterase," Biochem. Biophys. Acta, 429:485-497 (1976).
Hinshaw et al., "Survival of primates in LD100 septic shock following therapy with antibody to tumor necrosis factor (TNF alpha)," Circ. Shock, 30:279-292 (1990).
Holler et al., "Increased serum levels of tumor necrosis factor alpha precede major complications of bone marrow transplantation," Blood 75:1011-1016 (1990).
Huang et al., "Impact of solid state properties on developability assesment of drug candidates," Advanced Drug Delivery Reviews, 56(3):321-334 (2004).
Ich Harmonised Tripartite Guideline, Specifications: test procedures and acceptance criteria for new drug substances and new drug products: chemical substances Q6A, Current Step 4 version (Oct. 6, 1999) 36 pages.
International Search Report in Corresponding Application No. PCT/US2008/004021 dated Jan. 14, 2009.
Johnson et al., "Tumors producing human tumor necrosis factor induced hypercalcemia and osteoclastic bone resorption in nude mice," Endocrinology 124:1424-1427 (1989).
Jones et al., "Pharmaceutical Cocrystals: An Emerging Approach to Physical Property Enhancement," Mater. Res. Bull., 31:875-79 (2006).
Lai et al., "One-pot approach for the regioselective synthesis of beta-keto sufones based on acid-catalyzed reaction of sulfonyl chlorides with arylacetylenes and water," Tetrahedron Lett., 46(3):513-515 (2005).
List et al., "The myelodysplastic syndromes: biology and implications for management," J. Clin. Oncol. 8:1424-1441 (1990).
Liu et al., "Synthesis of enantiomerically pure N-tert-butanesulfinyl imines (tert-butanesulfinimines) by the direct condensation of tert-butanesulfinamide with aldehydes and ketones," J. Org. Chem. 64:1278-1284 (1999).
Lorenz et al., "Perspectives for TNF-α-targeting therapies," Arthritis Res., 4(suppl 3):S17-S24 (2002).
Lowe and Cheng, "The PDE IV family of calcium-independent phosphodiesterase enzymes," Drugs of the Future, 17(9):799-807 (1992).
Lowe et al., "Novel dioxolanes as cholesterol lowering agents," Exp. Opin. Ther. Patents 8(10):1309-1332 (1998).
Luke et al., "Synthesis of (S)-5-(1-Aminoethyl)-2-(Cyclohexylmethoxy) Benzamide," Tetrahedron: Asymmetry, Elsevier Science Publishers, Amsterdam, NL, 10(22):4393-4403 (1999).
Marriott et al., "Immunotherapeutic and Antitumour Potential of Thalidomide Analogues," Expert Opin. Biol. Ther. 1(4):1-8 (2001).
Marriott et al., "Thalidomide and Its Analogues Have Distinct and Opposing Effects on TNF-Alpha and TNFR2 During Co-Stimulation of Both CD4(+) and CD8(+) T cells," Clin. Exp. Immunol. 130(1):75-84 (2002).
Merck Manual, 17th ed., 953 (1999).
Millar et al., "Tumour necrosis factor in bronchopulmonary secretions of patients with adult respiratory distress syndrome," Lancet, 2(8665):712-714 (1989).
Molostvov et al., "The Effects of Selective Cytokine Inhibitory Drugs (CC-10004 and CC-1088) on VEGF and IL-6 Expression and Apoptosis in Myeloma and Endothelial Cell Co-Cultures," Br. J. Haematol.124(3):366-375 (2004).
Monté et al., "Productive human immunodeficiency virus-1 infection of megakaryocytic cells is enhanced by tumor necrosis factor-alpha," Blood 79:2670-2679 (1992).
Muller et al., "Amino-substituted thalidomide analogs: potent inhibitors of TNF-alpha production," Bioorg. Med. Chem. Lett., 9:1625-1630 (1999).
Muller et al., "Structural modifications of thalidomide produce analogs with enhanced tumor necrosis factor inhibitory activity," J. Med. Chem. 39:3238-3240 (1996).
Muller et al., "Thalidomide analogs and PDE4 inhibition," Bioorg. & Med Chem Lett., 8:2669-2674 (1998).

(56) References Cited

OTHER PUBLICATIONS

Nicholson et al., "Differential modulation of tissue function and therapeutic potential of selective inhibitors of cyclic nucleotide phosphodiesterase isoenzymes," Trends Pharmaco. Sci., 12:19-27 (1991).
Non-Final Office Action dated Jun. 16, 2010 in U.S. Appl. No. 12/079,615.
Non-Final Office Action dated Mar. 18, 2013 in U.S. Appl. No. 13/300,458.
Notice of Allowance dated Oct. 20, 2010 in U.S. Appl. No. 12/079,615.
Notice of Allowance dated Sep. 23, 2013 in U.S. Appl. No. 13/300,458.
Notice of Opposition (LEK), for EP Patent No. 2276483, dated Feb. 9, 2015.
Notice of Opposition (Polpharma) dated Feb. 6, 2015, in Opposition of EP Patent No. 2276483.
Notice of Opposition (Teva) dated Febmary 6, 2015, in Opposition of EP Patent No. 2276483.
Notice of Opposition (Zentiva k.s.), dated Feb. 6, 2015, in Opposition of EP Patent No. 2276483.
Notice of Opposition dated May 26, 2010, in Opposition of EP Patent No. 1485087.
Notice of References Cited from Office Action dated Dec. 3, 2007 in U.S. Appl. No. 11/106,142.
Opponent's Response to Grounds of Appeal, dated Feb. 3, 2012, in Opposition of EP Patent No. 1485057.
Opponent's response to Summons to attend Oral Proceedings dated Feb. 3, 2015, in Opposition to EP Patent No. 1485087.
Papp et al., "Oral apremilast is active in the treatment of moderate to severe placque psoriasis," J. Am. Acad. Dermatol., p. 3308 (2011).
Patentee's Grounds of Appeal, dated Sep. 19, 2011, in Opposition of EP Patent No. 1485087.
Patentee's Petition for Review by Enlarged Appeal Board, dated Sep. 30, 2015, in Opposition to EP Patent No. 1485087.
Patentee's Response dated Jun. 25, 2012, in Opposition of EP Patent No. Patent No. 1485057; and revised Annex A, dated Jan. 16, 2013.
Patentee's Response to Notice of Opposition dated Oct. 29, 2010, in Opposition of EP Patent No. 1485087.
Patentee's Response to Summons to attend Oral Proceedings dated Feb. 16, 2015, in Opposition of EP Patent No. 1485087.
Patentee's Reply to the Notices of Opposition dated Sep. 23, 2015, in Opposition of EP Patent No. 2276483.
Patentee's Response to Summons to attend oral proceedings, dated Oct. 25, 2013, in Opposition of EP Patent No. 2276483.
Piguet et al., "Requirement of tumour necrosis factor for development of silica-induced pulmonary fibrosis," Nature, 344(6263):245-247 (1990).
Poli et al., "The Effect of Cytokines and Pharmacologic Agents on Chronic HIV Infection," AIDS Res. Hum. Retrovirus, 8(2)191-197 (1992).
Poli et al., Tumor necrosis factor alpha functions in an autocrine manner in the induction of human immunodeficiency virus expression, Proc. Natl. Acad. Sci USA, 87(2):782-785 (1990).
Poole et al., "Apremilast: first global approval," Drugs, 825-837 (2014).
Ratziu et al., "Lack of efficacy of an inhibitor of PDE4 in phase 1 and 2 trials of patients with nonalcoholic steatohepatitis," Clin. Gastroenterol. Hepatol., 12(10):1724-1730 (2014).
Rice and Bevilacqua, "An inducible endothelial cell surface glycoprotein mediates melanoma adhesion," Science, 246(4935):1303-1306 (1989).
Schafer et al., "Apremilast, a cAMP phosphodiesterase-4 inhibitor, demonstrates anti-inflammatory activity in vitro and in a model of psoriasis," Br. J. Pharmacol., 159(4):842-855 (2010).
Shealy et al., "D- and L-thalidomide," Chem. Indus. 12;24:1030-1031 (1965).
Simonyi et al., "Stereochemical Aspects of Drug Action. II: Optical Isomerism," in The Practice of Medicinal Chemistry, Ed. Wermuth, Academic Press, London, Chapter 21 (1996).
STN Accession No. 1967:75462 (1966).
Strand et al., "Improvede quality of life with apremilast (APR) in the treatment of psoriasis: results from a phase IIb randomized controlled study," J. Am. Acad. Dermatol., p. 3337 (2011).
Summary of Product Characteristics (Otezla) dated Feb. 16, 2015.
Tencer et al., "Economic evaluation of sequencing strategies in the treatment of moderate to severe psoriasis in the United States," EADV (2014).
The Merck Manual, 17$^{th}$ Edition, Merck & Company, West Point, PA, pp. 448 (1999).
Tierney et al., Current Medical Diagnosis & Treatment, 37$^{th}$ ed., Appleton & Lange, p. 499 (1998).
Tracey et al., "Anti-cachectin/TNF monoclonal antibodies prevent septic shock during lethal bacteraemia," Nature, 330:662-664 (1987).
Trask et al., "Selective Polymorph Transformation Via Solvent-Drop Grinding," Chem. Commun., 880-882 (2005).
U.S. Department of Health and Human Services, Food and Drug Administration, "Guidance for Industry—Impurities: Residual Solvents in New Veterinary Medicinal Products, Active Substances and Excipients," pp. 1-20 (2000).
Van Dullemen et al., "Treatment of Crohn's disease with anti-tumor necrosis factor chimeric monoclonal antibody (cA2)," Gastroenterology, 109:129-135 (1995).
Velasquez et al.,. "Stereoselective synthesis of β-substituted β-amino sulfones and sulfonamides via addition of sulfonyl anions to chiral N-sulfinyl imines," Organic Lett., 8(4):789-792 (2006).
Verghese et al., "Regulation of ion transport by endothelins in rat colonic mucosa: effects of an ETA antagonist (FR139317) and an ETB agonist (IRL1620)," J. Pharmacol. Exp. Ther., 272(3): 1313-1320 (1995).
Vippagunta et al., "Crystalline solids," Adv. Drug Deliv. Rev., 48:3-26 (2001).
Wilen et al., "Strategies in optical resolutions," Tetrahedron 33:2725-2736 (1977).
Wilen, Tables of Resolving Agents and Optical Resolutions (E.L. Eliel, Ed., Univ. of Notre Dame Press, Notre Dame, IN) p. 268 (1972).
Wolff, Manfred E., ed., "Burger's Medicinal Chemistry and Drug Discovery," 5$^{th}$ ed., 172-178, 949-982 (1995).
Yu, "Amorphous pharmaceutical solids: preparation, characterization and stabilization," Adv. Drug Deliv. Rev., 48:27-42 (2001).
Zhang et al., "Practical and stereoselective synthesis of β-amino sulfones from alkyl phenyl sulfones and N-(tert-butylsulfinyl) aldimines," Org. Biomol. Chem., 9:6502-6505 (2011).

* cited by examiner

APREMILAST FOR THE TREATMENT OF A LIVER DISEASE OR A LIVER FUNCTION ABNORMALITY

The present application is a 35 USC § 371 national stage application of International Application No. PCT/US2015/036898, filed Jun. 22, 2015, which claims the benefit of U.S. Provisional Application No. 62/016,013, filed Jun. 23, 2014, the contents of which are hereby incorporated by reference.

1. FIELD

Provided herein are methods for treating, preventing and/or managing a liver disease or a liver function abnormality by the administration of apremilast, alone or in combination with other therapeutics or treatment regimens. Also provided herein are pharmaceutical compositions and dosage forms comprising specific amounts of apremilast suitable for use in methods of treating, preventing and/or managing a liver disease or a liver function abnormality.

2. BACKGROUND

Fatty liver disease (FLD), whether it is alcoholic FLD (AFLD) or nonalcoholic FLD (NAFLD), encompasses a morphological spectrum of hepatic steatosis (fatty liver) and steatohepatitis. Alcohol is a well-known cause of fatty liver disease in adults, and can manifest histologically as steatosis, steatohepatitis, and cirrhosis. In recent years it has become evident that another entity, nonalcoholic fatty liver disease (NAFLD), can mimic the entire spectrum of hepatic changes typically associated with alcohol abuse. NAFLD is associated with insulin resistance, obesity, diabetes mellitus, hypertension, and dyslipidemias, collectively called the metabolic syndrome. The morphologic changes of alcoholic and nonalcoholic fatty liver disease are indistinguishable (Kumar, Abbas, Aster, *Robbins Basic Pathology*, $9^{th}$ Ed.; Elsevier; 2013).

NAFLD is a condition defined by excessive fat accumulation in the form of triglycerides (steatosis) in the liver (>5% of hepatocytes histologically). A subgroup of NAFLD patients have liver cell injury and inflammation in addition to excessive fat (steatohepatitis). The latter condition, designated nonalcoholic steatohepatitis (NASH), is virtually indistinguishable histologically from alcoholic steatohepatitis (ASH). While the simple steatosis seen in NAFLD does not correlate with increased short-term morbidity or mortality, progression of this condition to that of NASH dramatically increases the risks of cirrhosis, liver failure, and hepatocellular carcinoma (HCC). Cirrhosis due to NASH is an increasingly frequent reason for liver transplantation (Global Guidelines—Nonalcoholic Fatty Liver Disease and Nonalcoholic Steatohepatitis, World Gastroenterology Organisation, June 2012).

NASH is widely considered to be the liver expression of the metabolic syndrome. There is at present a worldwide epidemic of diabetes and obesity. At least 1.46 billion adults were overweight or obese and 170 million of the world's children were overweight or obese in 2008. The numbers are continuing to rise, indicating that NASH will become an increasingly common liver problem in both rich and poor countries, increasing the global burden of liver disease, and affecting public health and health-care costs globally.

Over the past couple of decades, it has become increasingly clear that NAFLD and NASH are now the number one cause of liver disease in Western countries. The prevalence of NAFLD has doubled during last 20 years, whereas the prevalence of other chronic liver diseases has remained stable or even decreased. More recent data confirm that NAFLD and NASH play an equally important role in the Middle East, Far East, Africa, the Caribbean, and Latin America.

PDE4 inhibitors have been evaluated in NAFLD with mixed results. Pentoxifylline appears to improve Liver Function Tests abnormalities by decreasing levels of alanine aminotransferase and/or aspartate aminotransferase (ALT and AST respectively) in both animal models and human studies without effecting cytokines such as TNF-α (Chae M K et al. *Exp Diabetes Res* 2012; 762565). However, in a Phase 1 clinical trial of ASP9831 by Astellas, after 12 weeks of treatment neither a 50 mg nor 100 mg daily dose demonstrated any significant difference in percentage change from baseline for either AST or ALT (Ratziu V, et al. *Clin Gastroenterol Hepatol*. 2014 Feb. 12. pii: S1542-3565). Thus, there remains a clear and unmet need to develop therapeutics for more effective treatment of liver disease and liver function abnormalities.

Other liver diseases having liver function abnormalities include inherited liver disorders (e.g. porphyria, Wilson's disease, and hemachromatosis); acute hepatitis (viral or bacterial infection, toxin exposure, and drug-induced hepatitis); autoimmune liver disease (e.g. primary biliary cirrhosis and lupus hepatitis); and biliary tract disease (e.g. sclerosing cholangitis). These diseases and pruritus associated with liver disease may benefit from treatment with a selective PDE4 inhibitor.

3. SUMMARY

Provided herein are methods for treating, preventing and/or managing a liver disease or a liver function abnormality in humans in need thereof. Liver diseases having liver function abnormalities include, but are not limited to, inherited liver disorders (e.g. porphyria, Wilson's disease, and hemachromatosis); acute hepatitis (viral or bacterial infection, toxin exposure, and drug-induced hepatitis); autoimmune liver disease (e.g. primary biliary cirrhosis and lupus hepatitis); and biliary tract disease (e.g. sclerosing cholangitis). Additionally, herein are methods for treating pruritus associated with liver disorders and jaundice. The methods comprise administering to a patient in need of such treatment, prevention or management with a therapeutically or prophylactically effective amount of apremilast, or a pharmaceutically acceptable prodrug, metabolite, polymorph, salt, solvate (e.g., hydrate) or clathrate thereof. Also provided herein is a therapeutically or prophylactically effective amount of a compound being apremilast, or a pharmaceutically acceptable prodrug, metabolite, polymorph, salt, solvate (e.g., hydrate) or clathrate thereof for use in methods as described above, wherein the methods comprise administering to a patient in need of such treatment, prevention or management the compound.

In some embodiments, provided herein is a method of treating, preventing and/or managing a liver disease or a liver function abnormality, which comprises orally administering to a patient having a liver disease or a liver function abnormality an effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof. In some embodiments, provided herein is an effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof, for use in a method of treating, preventing and/or managing a liver disease or a liver function abnormality, which comprises orally administering to a patient having a liver disease or a liver function abnormality an effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof. In some embodiments, the compound of the invention is administered once daily. In some embodiments, the compound of the invention is administered twice daily.

In some embodiments, the patient is administered about 10 mg twice daily (BID) of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof. In some embodiments, the dose is about 20 mg BID. In other embodiments, the dose is about 30 mg BID. In some embodiments, the dose is about 40 mg BID or 80 mg once daily (QD).

In some embodiments, stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof is administered orally in a dosage form such as a tablet or a capsule.

4. DETAILED DESCRIPTION

4.1 Definitions

As used herein, the term "apremilast" refers to (+)-2-[1-(3-ethoxy-4-methoxyphenyl)-2-methylsulfonylethyl]-4-acetylaminoisoindoline-1,3-dione, also known as N-[2-[(1S)-1-(3-ethoxy-4-methoxylphenyl)-2-(methylsulfonyl)ethyl]-2,3-dihydro-1,3-dioxo-1H-isoindol-4-yl]acetamide. Apremilast has the following structure:

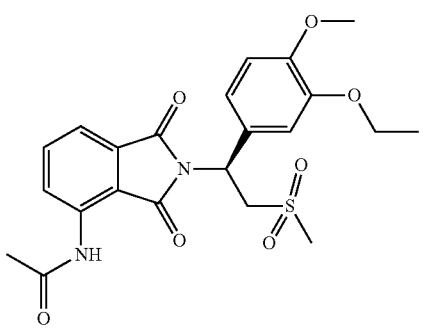 [SMILES: CCOc1cc([C@@H](CS(C)(=O)=O)N2C(=O)c3cccc(NC(C)=O)c3C2=O)ccc1OC]

Without being limited by theory or mechanism of action, apremilast is an inhibitor of phosphodiesterase 4 (PDE4), and works intracellularly to modulate a network of pro- and anti-inflammatory mediators. Phosphodiesterase 4 is a cyclic adenosine monophosphate (cAMP)-specific phosphodiesterase (PDE) and the dominant PDE in inflammatory cells. Inhibition of PDE4 elevates intracellular cAMP levels, which in turn down regulates the inflammatory response by modulating the expression of tumor necrosis factor-alpha (TNF-α), interleukin (IL)-23, and other inflammatory cytokines. Elevation of cAMP also increases anti inflammatory cytokines such as IL-10. These pro- and anti-inflammatory mediators have been implicated in psoriasis and psoriatic arthritis. See, e.g., Schafer et al., "Apremilast, a cAMP phosphodiesterase-4 inhibitor, demonstrates anti-inflammatory activity in vitro and in a model of psoriasis," *Br. J. Pharmacol.*, 2010, 159(4):842-55.

Apremilast is under clinical development for the treatment of adult inflammatory autoimmune disorders that involve elevated cytokine levels, such as psoriasis, psoriatic arthritis, rheumatoid arthritis, Behçet's disease and ankylosing spondylitis.

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts provided herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of apremilast that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by *Burger's Medicinal Chemistry and Drug Discovery*, 172-178, 949-982 (Manfred E. Wolff ed., 5th ed. 1995).

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 90%, 95%, 96%, 97%, 98% or 99% of one stereoisomer, and 20%, 10%, 5%, 4%, 3%, 2%, 1% or less of the counter stereoisomer. "Substantially free of its (R) enantiomer" is encompassed by the term stereomerically pure or enantiomerically pure.

As used herein, term "adverse effect" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein, the term "patient" refers to a mammal, particularly a human. In some embodiments, the patient is a female. In further embodiments, the patient is a male. In further embodiments, the patient is a child or adolescent.

As used herein, and unless otherwise specified, the term "liver function abnormality" includes, but is not limited to, a liver disease or abnormality that can result in an abnormal liver function test. An abnormal liver function test may indicate abnormal levels of bilirubin, albumin, total protein, lactic dehydrogenase, alkaline phosphatase, 5'-nucleotidase, gamma glutamyltranspeptidase, aminotransferases and other enzymes in the blood. Liver function tests are known in the art, see e.g., Lee, *Basic Skills in Interpreting Laboratory Data*, 5$^{th}$ Ed., American Society of Health-System Pharmacists 2013.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression of symptoms of the disease or disorder.

As used herein, unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing," and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

4.2 Methods of Treatment

Provided herein are methods of treating, managing and/or preventing a liver disease or a liver function abnormality, which comprise administering to a patient in need of such treatment, management or prevention a therapeutically or prophylactically effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate or clathrate thereof. Liver diseases having liver function abnormalities include, but are not limited to, inherited liver disorders (e.g. porphyria, Wilson's disease, and hemachromatosis); acute hepatitis (viral or bacterial infection, toxin exposure, and drug-induced hepatitis); autoimmune liver disease (e.g. primary biliary cirrhosis and lupus hepatitis); and biliary tract disease (e.g. sclerosing cholangitis).

In some embodiments, the methods also encompass inhibiting or averting symptoms of a liver disease or a liver function abnormality as well as addressing the disease itself, prior to the onset of symptoms by administering stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate or clathrate thereof.

In one embodiment provided herein is a method of treating or managing a liver disease or a liver function abnormality, which comprises orally administering to a patient having a liver disease or a liver function abnormality an effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof.

In one embodiment provided herein is a method of treating or managing pruritus associated with a liver disease or a liver function abnormality, which comprises orally administering to a patient having a liver disease or a liver function abnormality an effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof.

In one embodiment, stereomerically pure (+)-2-[1-(3-ethoxy-4-methoxyphenyl)-2-methylsulfonylethyl]-4-acetylaminoisoindoline-1,3-dione is administered once daily. In one embodiment, stereomerically pure (+)-2-[1-(3-ethoxy-4-methoxyphenyl)-2-methylsulfonylethyl]-4-acetylaminoisoindoline-1,3-dione is administered twice daily. In some embodiments, stereomerically pure (+)-2-[1-(3-ethoxy-4-methoxyphenyl)-2-methylsulfonylethyl]-4-acetylaminoisoindoline-1,3-dione is administered in an amount of about 10 mg, 20 mg, 30 mg, or 40 mg once daily. In certain embodiments, stereomerically pure (+)-2-[1-(3-ethoxy-4-methoxyphenyl)-2-methylsulfonylethyl]-4-acetylaminoisoindoline-1,3-dione may be used alone in doses of 10, 20 mg, 30 mg, or 40 mg once daily, or in combination with other treatment measures. In some embodiments, stereomerically pure (+)-2-[1-(3-ethoxy-4-methoxyphenyl)-2-methylsulfonylethyl]-4-acetylaminoisoindoline-1,3-dione is administered in an amount of about 10 mg, 20 mg, 30 mg, or 40 mg twice daily. In certain embodiments, stereomerically pure (+)-2-[1-(3-ethoxy-4-methoxyphenyl)-2-methylsulfonylethyl]-4-acetylaminoisoindoline-1,3-dione may be used alone in doses of 10, 20 mg, 30 mg, or 40 mg twice daily (BID), or in combination with other treatment measures.

In one embodiment, stereomerically pure (+)-2-[1-(3-ethoxy-4-methoxyphenyl)-2-methylsulfonylethyl]-4-acetylaminoisoindoline-1,3-dione is administered in an amount of about 100 mg once daily. In one embodiment, stereomerically pure (+)-2-[1-(3-ethoxy-4-methoxyphenyl)-2-methylsulfonylethyl]-4-acetylaminoisoindoline-1,3-dione is administered in an amount of about 90 mg once daily. In one embodiment, stereomerically pure (+)-2-[1-(3-ethoxy-4-methoxyphenyl)-2-methylsulfonylethyl]-4-acetylaminoisoindoline-1,3-dione is administered in an amount of about 80 mg once daily. In one embodiment, stereomerically pure (+)-2-[1-(3-ethoxy-4-methoxyphenyl)-2-methylsulfonylethyl]-4-acetylaminoisoindoline-1,3-dione is administered in an amount of about 70 mg once daily. In one embodiment, stereomerically pure (+)-2-[1-(3-ethoxy-4-methoxyphenyl)-2-methylsulfonylethyl]-4-acetylaminoisoindoline-1,3-dione is administered in an amount of about 60 mg once daily. In one embodiment, stereomerically pure (+)-2-[1-(3-ethoxy-4-methoxyphenyl)-2-methylsulfonylethyl]-4-acetylaminoisoindoline-1,3-dione is administered in an amount of about 50 mg once daily.

In one embodiment, the patient is administered about 10 mg BID of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof. In some embodiments, the dose is about 20 mg BID. In other embodiments, the dose is about 30 mg BID. In other embodiments, the dose is about 40 mg BID.

In one embodiment, the patient is administered about 10 mg QD of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof. In some embodiments, the dose is about 20 mg QD. In other embodiments, the dose is about 30 mg QD. In other embodiments, the dose is about 40 mg QD. In other embodiments, the dose is about 50 mg QD. In other embodiments, the dose is about 60 mg QD. In other embodiments, the dose is about 70 mg QD. In other embodiments, the dose is about 80 mg QD.

In one embodiment, stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof is administered orally in a dosage form such as a tablet or a capsule.

In one embodiment, stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof is administered orally in a tablet form. In some embodiments, the tablet comprises a 10 mg, 20 mg, 30 mg, or 40 mg dose of stereomerically pure (+)-2-[1-(3-ethoxy-4-methoxyphenyl)-2-methylsulfonylethyl]-4-acetylaminoisoindoline-1,3-dione.

In one embodiment, stereomerically pure (+)-2-[1-(3-ethoxy-4-methoxyphenyl)-2-methylsulfonylethyl]-4-acetylaminoisoindoline-1,3-dione is orally administered to a patient having a liver disease or a liver function abnormality at a starting dose of about 10 mg, 20 mg, 30 mg, or 40 mg twice daily. In some embodiments, the maximum daily dose is about 20 mg to about 40 mg. In some embodiments, the maximum daily dose is about 30 mg to about 60 mg. In some embodiments, the maximum daily dose is about 40 mg to about 100 mg.

In one embodiment, stereomerically pure (+)-2-[1-(3-ethoxy-4-methoxyphenyl)-2-methylsulfonylethyl]-4-acetylaminoisoindoline-1,3-dione is orally administered to a patient having a liver disease or a liver function abnormality at a starting dose of about 10 mg, 20 mg, 30 mg, or 40 mg once daily. In some embodiments, the maximum daily dose is about 20 mg to about 40 mg. In some embodiments, the maximum daily dose is about 30 mg to about 60 mg. In some embodiments, the maximum daily dose is about 40 mg to about 100 mg.

In one embodiment, the stereomerically pure (+)-2-[1-(3-ethoxy-4-methoxyphenyl)-2-methylsulfonylethyl]-4-acetylaminoisoindoline-1,3-dione comprises greater than about 90% by weight of (+) isomer based on the total weight percent of the compound.

In one embodiment, stereomerically pure (+)-2-[1-(3-ethoxy-4-methoxyphenyl)-2-methylsulfonylethyl]-4-acetylaminoisoindoline-1,3-dione comprises greater than about 95% by weight of (+) isomer based on the total weight percent of the compound.

In one embodiment, stereomerically pure (+)-2-[1-(3-ethoxy-4-methoxyphenyl)-2-methylsulfonylethyl]-4-acetylaminoisoindoline-1,3-dione comprises greater than about 96% by weight of (+) isomer based on the total weight percent of the compound.

In one embodiment, stereomerically pure (+)-2-[1-(3-ethoxy-4-methoxyphenyl)-2-methylsulfonylethyl]-4-acetylaminoisoindoline-1,3-dione comprises greater than about 97% by weight of (+) isomer based on the total weight percent of the compound.

In one embodiment, stereomerically pure (+)-2-[1-(3-ethoxy-4-methoxyphenyl)-2-methylsulfonylethyl]-4-acetylaminoisoindoline-1,3-dione comprises greater than about 98% by weight of (+) isomer based on the total weight percent of the compound.

In one embodiment, stereomerically pure (+)-2-[1-(3-ethoxy-4-methoxyphenyl)-2-methylsulfonylethyl]-4-acetylaminoisoindoline-1,3-dione comprises greater than about 99% by weight of (+) isomer based on the total weight percent of the compound.

In one embodiment, stereomerically pure (+)-2-[1-(3-ethoxy-4-methoxyphenyl)-2-methylsulfonylethyl]-4-acetylaminoisoindoline-1,3-dione is administered in an amount of about 20 mg twice a day following the initial titration schedule.

In one embodiment, stereomerically pure (+)-2-[1-(3-ethoxy-4-methoxyphenyl)-2-methylsulfonylethyl]-4-acetylaminoisoindoline-1,3-dione is administered in an amount of about 30 mg twice a day following the initial titration schedule.

In one embodiment, stereomerically pure (+)-2-[1-(3-ethoxy-4-methoxyphenyl)-2-methylsulfonylethyl]-4-acetylaminoisoindoline-1,3-dione is administered in an amount of about 40 mg twice a day following the initial titration schedule.

In one embodiment, stereomerically pure (+)-2-[1-(3-ethoxy-4-methoxyphenyl)-2-methylsulfonylethyl]-4-acetylaminoisoindoline-1,3-dione is administered once daily.

In one embodiment, stereomerically pure (+)-2-[1-(3-ethoxy-4-methoxyphenyl)-2-methylsulfonylethyl]-4-acetylaminoisoindoline-1,3-dione is administered twice daily.

In one embodiment, stereomerically pure (+)-2-[1-(3-ethoxy-4-methoxyphenyl)-2-methylsulfonylethyl]-4-acetylaminoisoindoline-1,3-dione is administered in a tablet form. In some embodiments, the tablet comprises a 10 mg, 20 mg, 30 mg, 40 mg or 80 mg dose of stereomerically pure (+)-2-[1-(3-ethoxy-4-methoxyphenyl)-2-methylsulfonylethyl]-4-acetylaminoisoindoline-1,3-dione.

In one embodiment, the tablet further comprises lactose monohydrate, microcrystalline cellulose, croscarmellose sodium, magnesium stearate, polyvinyl alcohol, titanium dioxide, polyethylene glycol, and talc. In one embodiment, the tablet further comprises iron oxide red. In one embodiment, the tablet further comprises iron oxide yellow. In one embodiment, the tablet further comprises iron oxide black.

In one embodiment, stereomerically pure (+)-2-[1-(3-ethoxy-4-methoxyphenyl)-2-methylsulfonylethyl]-4-acetylaminoisoindoline-1,3-dione is administered in a tablet form comprising a 10 mg dose of stereomerically pure (+)-2-[1-

(3-ethoxy-4-methoxyphenyl)-2-methylsulfonylethyl]-4-acetylaminoisoindoline-1,3-dione, lactose monohydrate, microcrystalline cellulose, croscarmellose sodium, magnesium stearate, polyvinyl alcohol, titanium dioxide, polyethylene glycol, talc, and iron oxide red.

In one embodiment, stereomerically pure (+)-2-[1-(3-ethoxy-4-methoxyphenyl)-2-methylsulfonylethyl]-4-acetylaminoisoindoline-1,3-dione is administered in a tablet form comprising a 20 mg dose of stereomerically pure (+)-2-[1-(3-ethoxy-4-methoxyphenyl)-2-methylsulfonylethyl]-4-acetylaminoisoindoline-1,3-dione, lactose monohydrate, microcrystalline cellulose, croscarmellose sodium, magnesium stearate, polyvinyl alcohol, titanium dioxide, polyethylene glycol, talc, iron oxide red, and iron oxide yellow.

In one embodiment, stereomerically pure (+)-2-[1-(3-ethoxy-4-methoxyphenyl)-2-methylsulfonylethyl]-4-acetylaminoisoindoline-1,3-dione is administered in a tablet form comprising a 30 mg dose of stereomerically pure (+)-2-[1-(3-ethoxy-4-methoxyphenyl)-2-methylsulfonylethyl]-4-acetylaminoisoindoline-1,3-dione, lactose monohydrate, microcrystalline cellulose, croscarmellose sodium, magnesium stearate, polyvinyl alcohol, titanium dioxide, polyethylene glycol, talc, and iron oxide red, iron oxide yellow, and iron oxide black.

In one embodiment provided herein, the method further comprises administering to the patient a therapeutically effective amount of one or more second active agents. In one embodiment, one or more second active agents are medications for treating a liver disease or liver function abnormality.

In one embodiment, the liver disease is fatty liver disease.
In one embodiment, the liver disease is hepatic fibrosis.
In one embodiment, the liver disease is hepatic steatosis.
In one embodiment, the liver disease is nonalcoholic steatohepatitis.
In one embodiment, the liver disease is alcoholic steatohepatitis.
In one embodiment, the liver disease is relapsed or refractory to a prior treatment.
In one embodiment, the fatty liver disease is nonalcoholic fatty liver disease.
In one embodiment, the fatty liver disease is alcoholic fatty liver disease.
In one embodiment, the nonalcoholic fatty liver disease is pediatric nonalcoholic fatty liver disease.
In one embodiment, the liver function abnormality comprises an elevated level of alanine aminotransferase or aspartate aminotransferase in the patient.
In one embodiment, the liver disease is viral hepatitis.
In one embodiment, the liver disease is bacterial hepatisis.
In one embodiment, the liver disease is acute hepatitis.
In one embodiment, the liver disease is primary biliary cirrhosis.
In one embodiment, the liver disease is lupus hepatitis.
In one embodiment, the liver disease is Wilson's disease.
In one embodiment, the liver disease is drug-induced hepatitis.
In one embodiment, the liver disease is toxin exposure hepatitis.
In one embodiment, the liver disease is hemochromatosis.
In one embodiment, the liver disease is acute porphyria.
In one embodiment, the liver disease is autoimmune hepatitis.
In one embodiment, the liver disease is sclerosis cholangitis.
In one embodiment, the liver disease is acute cholestatic jaundice.
In one embodiment, the liver disease is associated with pruritus.

In one embodiment, a normal range of aspartate aminotransferase is from 10 to 35 IU/L. In one embodiment, an elevated or high level of aspartate aminotransferase is greater than 35 IU/L. In one embodiment, a low level of aspartate aminotransferase is less than 10 IU/L.

In one embodiment, a normal range of alanine aminotransferase is from 10 to 40 IU/L. In one embodiment, an elevated or high level of alanine aminotransferase is greater than 40 IU/L. In one embodiment, an low level of alanine aminotransferase is less than 10 IU/L.

In one embodiment provided herein, the method comprises administering stereomerically pure (+)-2-[1-(3-ethoxy-4-methoxyphenyl)-2-methylsulfonylethyl]-4-acetylaminoisoindoline-1,3-dione, substantially free of any salt, solvate, or prodrug forms of (+)-2-[1-(3-ethoxy-4-methoxyphenyl)-2-methylsulfonylethyl]-4-acetylaminoisoindoline-1,3-dione.

In one embodiment provided herein, the method comprises administering a pharmaceutically acceptable salt of stereomerically pure (+)-2-[1-(3-ethoxy-4-methoxyphenyl)-2-methylsulfonylethyl]-4-acetylaminoisoindoline-1,3-dione.

In one embodiment provided herein, the method comprises administering a pharmaceutically acceptable solvate of stereomerically pure (+)-2-[1-(3-ethoxy-4-methoxyphenyl)-2-methylsulfonylethyl]-4-acetylaminoisoindoline-1,3-dione.

In one embodiment provided herein, the method decreases the level of alanine aminotransferase in the patient.

In one embodiment provided herein, the method decreases the level of aspartate aminotransferase in the patient.

In one embodiment, the methods further comprises the administration of a therapeutically or prophylactically effective amount of one or more second active agents, including but not limited to, an analgesic, an anti-inflammatory agent, a COX-2 inhibitor, an opioid, a corticosteroid, a biologic agent, and an immunosuppressant. In one embodiment, the second active agent is a non-steroidal anti-inflammatory drug (i.e., NSAID such as celecoxib, diclofenac, ibuprofen, indomethacin, meloxicam, naproxen, and piroxicam). In one embodiment, the second active agent is a disease-modifying antirheumatic drug (i.e., DMARD such as methotrexate, leflunomide, sulfasalazine and hydroxychloroquine).

In one embodiment, the patient has received prior treatment for a liver disease or a liver function abnormality. In some embodiments, the patient is relapsed or refractory to prior treatment.

4.2.1 Combination Therapy

In particular methods encompassed by this embodiment, stereomerically pure (+)-2-[1-(3-ethoxy-4-methoxyphenyl)-2-methylsulfonylethyl]-4-acetylaminoisoindoline-1,3-dione is administered in combination with another drug ("second active agent") for treating, managing and/or preventing a liver disease or a liver function abnormality.

In particular methods encompassed by this embodiment, stereomerically pure (+)-2-[1-(3-ethoxy-4-methoxyphenyl)-2-methylsulfonylethyl]-4-acetylaminoisoindoline-1,3-dione is administered in combination with an additional treatment for treating, managing and/or preventing a liver disease or a liver function abnormality.

In one embodiment, the additional treatment is surgical correction of the liver disease or a liver function abnormality.

In one embodiment, the additional treatment is a liver transplant.

In certain embodiments, the methods encompass synergistic combinations for the treatment, prevention and/or management of a liver disease or liver function abnormality. Stereomerically pure (+)-2-[1-(3-ethoxy-4-methoxyphenyl)-2-methylsulfonylethyl]-4-acetylaminoisoindoline-1,3-dione may also be used to alleviate adverse effects associated with some second active agents.

One or more second active agents can be used in the methods together with stereomerically pure (+)-2-[1-(3-ethoxy-4-methoxyphenyl)-2-methylsulfonylethyl]-4-acetylaminoisoindoline-1,3-dione. Second active agents can be administered before, after or simultaneously with stereomerically pure (+)-2-[1-(3-ethoxy-4-methoxyphenyl)-2-methylsulfonylethyl]-4-acetylaminoisoindoline-1,3-dione.

In some embodiments, the methods comprise the administration of a therapeutically effective amount of medications for treating a liver disease or liver function abnormality.

In one embodiment, the second active agent is selected from the group consisting of a thiazolidinedione, a statin, a fibrate, a lipid lowering agent, or a medication for weight loss. In one embodiment, the second active agent is a thiazolidinedione. In one embodiment, the second active agent is a statin. In one embodiment, the second active agent is a fibrate. In one embodiment, the second active agent is a lipid lowering agent. In one embodiment, the second active agent is a medication for weight loss.

In one embodiment, the second active agent is selected from the group consisting of an anti-inflammatory agent, an immunosuppressant, mycophenolate mofetil, a biologic agent, or a Cox-2 inhibitor. In one embodiment, the second active agent is an anti-inflammatory agent. In one embodiment, the second active agent is an immunosuppressant. In one embodiment, the second active agent is mycophenolate mofetil. In one embodiment, the second active agent is a biologic agent. In one embodiment, the second active agent is a Cox-2 inhibitor.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL, CHILDREN'S ADVIL/MOTRIN, MEDIPREN, MOTRIN, NUPRIN or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (DMARDs) or immnunosuppressants such as, but not limited to, methotrexate (Rheumatrex®), sulfasalazine (Azulfidine), leflunomide (Arava®), and cyclosporine (Sandimmune® or Neroal®).

In other embodiments, the second active agent is an oral corticosteroid, such as, but not limited to, budesonide (Entocort®), dexamethazone, fludrocortisone (Florinef®, Florinef® acetate), hydrocortisone, methylprednisone, prednisolone, and prednisone.

In other embodiments, second active agents may include, but are not limited to, mycophenolate mofetil (CellCept®), an immunosuppressive agent widely used in organ transplantation and gaining favor in treating autoimmune and inflammatory skin disorders.

In further embodiments, second active agents may include, but are not limited to, biologic agents such as etanercept (Enbrel®), infliximab (Remicade®) and adalimumab (Humira®).

In further embodiments, second active agents may include, but are not limited to, Cox-2 inhibitors such as celecoxib (Celebrex®), valdecoxib (Bextra®) and meloxicam (Mobic).

In some embodiments, one or more selective active agents are selected from the group consisting of acitretin, adalimumab, alclometasone, alefacept, aloe vera, amcinonide, ammonium lactate/urea, ammonium lactate/halobetasol, anthralin, benzocaine/pyrilamine/zinc oxide, betamethasone, betamethasone/calcipotriene, calcipotriene, clobetasol, clocortolone, coal tar, coal tar/salicylic acid, corticotropin, cyclosporine, desonide, desoximetasone, diflorasone, fluocinonide, flurandrenolide, halcinonide, halobetasol, hydrocortisone, hydrocortisone/pramoxine, hydroxyurea, infliximab, methotrexate, methoxsalen, mometasone, pramoxine, prednisone, prednisolone, prednicarbate, resorcinol, tazarotene, triamcinolone and ustekinumab.

In some embodiments, one or more selective active agents are selected from the group consisting of abatacept, acetaminophen, acetaminophen/hydrocodone, acetaminophen/tramadol, adalimumab, alemtuzumab, aluminum hydroxide/aspirin/calcium carbonate/magnesium hydroxide, anakinra, aspirin, auranofin, aurothioglucose, atorvastatin, azathioprine, celecoxib, certolizumab, chondroitin, cortisone, corticotropin, cyclophosphamide, cyclosporine, daclizumab, dexamethasone, diclofenac, diclofenac/misoprostol, diflunisal, doxycycline, esomeprazole, esomeprazole/naproxen, etanercept, etodolac, famotidine, famotidine/ibuprofen, fenoprofen, flurbiprofen, glucosamine, gold sodium thiomalate, golimumab, hydroxychloroquine, ibuprofen, indomethacin, infliximab, interferon, interferon gamma-1b, ketoprofen, lansoprazole, lansoprazole/naproxen, leflunomide, levamisole, meclofenamate, meloxicam, methotrexate, methylprednisone, methylprednisolone, methyl salicylate, minocycline, mycophenolate mofetil, nabumetone, naproxen, oxaprozin, penicillamine, phenytoin, piroxicam, prednisone, primrose oil, rituximab, rofecoxib, salsalate, sulindac, sulfasalazine, tetracycline, tocilizumab, tofacitinib, tolmetin, tramadol, triamcinolone, trolamine salicylate and valdecoxib.

In some embodiments, one or more selective active agents are selected from the group consisting of abatacept, acetaminophen, acetaminophen/hydrocodone, acetaminophen/tramadol, acitretin, adalimumab, alclometasone, alefacept, alemtuzumab, aloe vera, aluminum hydroxide/aspirin/calcium carbonate/magnesium hydroxide, amcinonide, ammonium lactate/urea, ammonium lactate/halobetasol, anakinra, anthralin, aspirin, auranofin, aurothioglucose, atorvastatin, azathioprine, benzocaine/pyrilamine/zinc oxide, betamethasone, betamethasone/calcipotriene, calcipotriene, celecoxib, certolizumab, chondroitin, clobetasol, clocortolone, coal tar, coal tar/salicylic acid, corticotropin, cortisone, cyclophosphamide, cyclosporine, daclizumab, desonide, desoximetasone, dexamethasone, diclofenac, diclofenac/misoprostol, diflorasone, diflunisal, doxycycline, esomeprazole, esomeprazole/naproxen, etanercept, etodolac, famotidine, famotidine/ibuprofen, fenoprofen, fluocinonide, flurandrenolide, flurbiprofen, fostamatinib, glucosamine, gold sodium thiomalate, golimumab, halcinonide, halobetasol, hydrocortisone, hydrocortisone/pramoxine, hydroxyurea, hydroxychloroquine, ibuprofen, indomethacin, infliximab, interferon, interferon gamma-1b, ibrutinib, ketoprofen, lansoprazole, lansoprazole/naproxen, leflunomide, lenalidomide, levamisole, meclofenamate, meloxicam, methotrexate, methoxsalen, methylprednisone, methylprednisolone, methyl salicylate, minocycline, mometasone, mycophenolate mofetil, nabumetone, naproxen, oxaprozin, penicillamine, phenytoin, piroxicam, pomalidomide, pramoxine, prednisone, prednisolone, prednicarbate, primrose oil, resorcinol, rituximab, rofecoxib, salsalate, sulindac, sulfasalazine, tazarotene, tetracycline, tocilizumab, tofacitinib, tolmetin, tramadol, triamcinolone, trolamine salicylate, ustekinumab, valdecoxib, 3-(5-amino-2-methyl-4-oxo-4H-quinazolin-3-yl)-piperidine-2,6-dione, and (S)-3-(4-((4-(morpholinomethyl)benzyl)oxy)-1-oxoisoindolin-2-yl)piperidine-2,6-dione.

In some embodiments, one or more selective active agents are selected from the group consisting of a Btk inhibitor, a cereblon targeting agent, a Tyk2 inhibitor, a Syk inhibitor, a JNK inhibitor, a MK2 inhibitor, a ERP5 inhibitor, a PD-1 inhibitor, a TIMP-3 inhibitor, a IKK-2 inhibitor, a LH2B inhibitor, a PKC-theta inhibitor, a IRAK4 inhibitor, a ROCK inhibitor, and a ROR-gamma-T inhibitor.

Administration of stereomerically pure (+)-2-[1-(3-ethoxy-4-methoxyphenyl)-2-methylsulfonylethyl]-4-acetylaminoisoindoline-1,3-dione and a second active agent to a patient can occur simultaneously or sequentially by the same or different routes of administration. The suitability of a particular route of administration employed for a particular second active agent will depend on the second active agent itself (e.g., whether it can be administered orally or topically without decomposition prior to entering the blood stream) and the subject being treated. Particular routes of administration for the second active agents or ingredients are known to those of ordinary skill in the art. See, e.g., *The Merck Manual*, 448 (17th ed., 1999).

The amount of a second active agent administered can be determined based on the specific agent used, the subject being treated, the severity and stage of disease and the amount(s) of stereomerically pure (+)-2-[1-(3-ethoxy-4-methoxyphenyl)-2-methylsulfonylethyl]-4-acetylaminoisoindoline-1,3-dione and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* (59th Ed., 2005).

In certain embodiments, the second active agent is administered orally, topically, intravenously or subcutaneously and once to four times daily in an amount of from about 1 to about 1,000 mg, from about 5 to about 500 mg, from about 10 to about 350 mg or from about 50 to about 200 mg. The specific amount of the second active agent will depend on the specific agent used, the age of the subject being treated, the severity and stage of disease and the amount(s) of stereomerically pure (+)-2-[1-(3-ethoxy-4-methoxyphenyl)-2-methylsulfonylethyl]-4-acetylaminoisoindoline-1,3-dione and any optional additional second active agents concurrently administered to the patient.

4.3 Apremilast

Without being limited by theory, apremilast is believed to be the (+) enantiomer of 2-[1-(3-ethoxy-4-methoxyphenyl)-2-methanesulfonylethyl]-4-acetylaminoisoindolin-1,3-dione having the following structure:

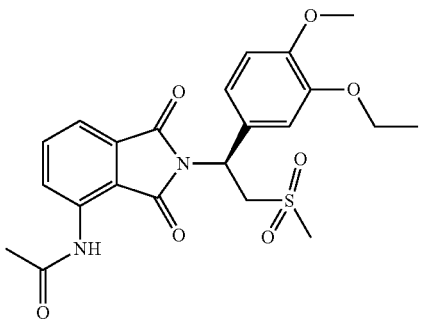 [SMILES: CCOc1cc([C@@H](CS(C)(=O)=O)N2C(=O)c3cccc(NC(C)=O)c3C2=O)ccc1OC]

Apremilast may be prepared according to methods disclosed in U.S. Pat. Nos. 6,962,940; 7,208,516; 7,427,638; or 7,893,101, the entirety of each which is incorporated herein by reference. In a specific method, apremilast may be prepared, for example, by the following process.

A stirred solution of 1-(3-ethoxy-4-methoxyphenyl)-2-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ: 1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CH), 3.85 (s, 3H, CH3), 4.11 (q, J=7 Hz, 2H, CH$_2$), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ: 14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for C$_{22}$H$_{24}$NO$_7$S: C, 57.38; H, 5.25; N, 6.08. Found: C, 57.31; H, 5.34; N, 5.83.

Preparation of 3-aminophthalic acid: 10% Pd/C (2.5 g), 3-nitrophthalic acid (75.0 g, 355 mmol) and ethanol (1.5 L) were charged to a 2.5 L Parr hydrogenator under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (br, s, 2H); $^{13}$C-NMR (DMSO-d6) δ: 112.00, 115.32, 118.20, 131.28, 135.86, 148.82, 169.15, 170.09.

Preparation of 3-aminophthalic anhydride: A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to about 25° C. and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

Resolution of 2-(3-ethoxy-4-methoxyphenyl-1-(methylsulphonyl)-eth-2-ylamine: A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$ @ pH 7.0, Ultron Chiral ES-OVS from Agilent Technologies, 150 mm×4.6 mm, 0.5 mL/min., @ 240 nm): 18.4 min (S-isomer, 99.2%), 25.5 min (R-isomer, 0.8%).

Final preparation of apremilast: A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g, 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of apremilast with 98% ee. Chiral HPLC (15/85 EtOH/20 mM KH$_2$PO$_4$ @ pH 5, Ultron Chiral ES-OVS from Agilent Technology, 150 mm×4.6 mm, 0.4 mL/min, @ 240 nm): 25.4 min (5-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H); $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

4.4 Pharmaceutical Compositions and Dosage Forms

Pharmaceutical compositions can be used in the preparation of individual, single unit dosage forms. Pharmaceutical compositions and dosage forms can comprise apremilast or a pharmaceutically acceptable salt or solvate thereof and a second active agent. Examples of the optional second active agents are disclosed herein (see, e.g., section 4.2.1). Pharmaceutical compositions and dosage forms can further comprise one or more carriers, excipients or diluents.

The pharmaceutical compositions provided herein are suitable for oral administration can be presented as discrete dosage forms, such as, but not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences,* 20th ed., Mack Publishing, Easton Pa. (2000).

Typical oral dosage forms are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, micro-crystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include, but are not limited to, the materials sold as AVICEL® (microcrystalline cellulose) PH-101, AVICEL® (microcrystalline cellulose) PH-103, AVICEL RC-581® (crystalline cellulose and carboxymethylcellulose sodium), AVICEL® (microcrystalline cellulose) PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581® (crystalline cellulose and carboxymethylcellulose sodium). Suitable anhydrous or low moisture excipients or additives include AVICEL-PH-103™® (microcrystalline cellulose) PH-103 and Starch 1500® LM (pregelatinized starch).

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200® (silica), manufactured by W.R. Grace Co. of Baltimore, Md.), a coagulated aerosol of synthetic silica (marketed by Degussa Co. of Plano, Tex.), CAB-O-SIL® (fumed silica) (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

Non-limiting examples of dosage forms include tablets; caplets; capsules, such as soft elastic gelatin capsules; sachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or water-in-oil emulsions), solutions and elixirs.

The composition, shape and type of dosage forms will typically vary depending on their use. For example, a dosage form used in the acute treatment of a disease may contain larger amounts of one or more of the active ingredients it comprises than a dosage form used in the chronic treatment of the same disease. These and other ways in which specific dosage forms will vary from one another will be readily apparent to those skilled in the art. See, e.g., *Remington's Pharmaceutical Sciences,* 20th ed., Mack Publishing, Easton Pa. (2,000).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition.

In certain embodiments, provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical oral dosage forms comprise apremilast in an amount of 10 mg, 20 mg, 30 mg, or 40 mg. In a particular embodiments, the oral dosage forms are 10 mg, 20 mg, 30 mg, or 40 mg tablets.

4.5 Delayed Release Dosage Forms

In certain embodiments, active ingredients can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients. In certain embodiments, provided herein are single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

5. EXAMPLES

Some embodiments are illustrated by the following non-limiting examples. The examples should not be construed as a limitation in the scope thereof.

5.1 Biological Activity of Apremilast in Preclinical Models

Arthritic conditions are considered to be a Th1 autoimmune disease because of the involvement of pro-inflammatory cytokines, interferon (INF)γ and tumor necrosis factor (TNF)-α. Elevation of cyclic nucleotide adenosine 3',5'-cyclic monophosphate (cAMP) inhibits the release of inflammatory mediators, including TNF-α. A cellular mechanism for the inactivation of cAMP is its breakdown by cyclic nucleotide phosphodiesterases (PDEs). The inhibition of PDE4 is particularly effective in the inhibition of inflammatory mediator release. Thus, compounds that inhibit PDE4 specifically may inhibit inflammation with a minimum of unwanted side effects.

Inhibition of TNF-α:

Apremilast inhibits TNF-α production in PBMCs ($IC_{50}$ of 77 nM), in human whole blood ($IC_{50}$ of 294), and in a mouse model ($EC_{50}$ of 0.05 mg/kg). The test methods were as described in WO 03/080049; Muller et al., *J. Med. Chem.*, 1996, 39:3238; and Muller et al., *Bioorg. Med. Chem. Lett.*, 1999, 9:1625-30.

Inhibition of PDE4:

Phosphodiesterase 4 enzyme was purified from U937 human monocytic cells by gel filtration chromatography, and phosphodiesterase reactions were carried out as previously described. See Muller et al., *Bioorg. Med. Chem. Lett.*, 1998, 8(19): 2669-2674. Briefly, reactions were carried out in 96-well deep-well plates in 50 mM Tris HCl pH 7.5, 5 mM $MgCl2$, 1 μM cyclic adenosine monophosphate (cAMP), plus 10 nM [3H]-cAMP for 45 min at 30° C. The reactions were terminated by boiling, treated with 1 mg/ml snake venom, and separated using AG-1X8 ion exchange resin (BioRad). Reactions consumed less than 15% of available substrate. Apremilast inhibited PDE4 with an $IC_{50}$ of 73.5 nM.

PDE4 Selectivity:

Apremilast selectively inhibits PDE4 over PDE1 (23% inhibition at 10 μM), PDE2 (6% inhibition at 10 μM), PDE3 (20% inhibition at 10 μM), PDE5 (3% inhibition at 10 μM), PDE6 (−6% inhibition at 10 μM) and PDE7 ($IC_{50}$ of 20.5 μM). PDE1, 2, 3 and 5 enzyme assays were prepared as described by Hidaka and Asano. Biochem. *Biophys. Acta.*, 1976, 429:485; see also Nicholsen et al., *Trends Pharmaco. Sci.*, 1991, 12:19. The PDE6 enzyme assay was prepared according to Baehr et al., *J. Biol. Chem.*, 1979, 254:11669 and Gillespie et al., *Mol. Pharm.*, 1989, 36: 773. The PDE7 enzyme assay was prepared according to Bloom and Beavo. *Proc. Natl. Acad. Sci. USA*, 1996, 93:14188-92.

5.2 Clinical Data of Treating or Managing a Liver Disease or a Liver Function Abnormality Using Apremilast (PALACE 1, 2, and 3)

Apremilast was studied in Phase 3 trials in both psoriatic arthritis and psoriasis patient populations and a Phase 2 trial in rheumatoid arthritis patients on background methotrexate. Patients in these studies showed improvement in liver functions as well as a reduction of liver function test (LFT) abnormalities. The improvement in mild baseline liver function test abnormalities has been observed with apremilast daily use without any prescribed changes in physical activity, social or dietary habits. The majority of the patient populations in both the psoriatic arthritis and psoriasis studies were overweight with the mean BMI for subjects greater than or equal to 30, more than half were consuming alcoholic beverages regularly, approximately 60% were taking methotrexate at an average dose of 15 mg daily, and 70% were using non-steroidal anti-inflammatory drugs (NSAIDs). Despite the balanced distribution of risk factors (both obesity and alcohol consumption are risk factors for fatty liver disease, and the use of NSAIDs and methotrexate increase the risk for liver function test abnormalities), the pooled populations had a similar number of subjects with abnormal LFTs at baseline. During the course of the study, there was observed a higher proportion of subjects in the apremilast treatment groups (both 20 mg BID and 30 mg BID) with normal LFTs (i.e. normal levels of ALT and AST)

at subsequent placebo-controlled study visits at week 4, week 16, and week 24 (See Tables 1 to 10 from PALACE 1, 2, and 3 studies).

Of the subjects tested for ALT at week 4, the 20 mg BID group showed a 8.7% increase in the number of patients with "normal" levels of ALT compared to the placebo group. At week 16, these patients showed a 12.4% increase in the number of patients with "normal" levels of ALT compared to the placebo group. At week 24, these patients showed a 14.9% increase in the number of patients with "normal" levels of ALT compared to the placebo group. See Table 1.

Of the subjects tested for ALT at week 4, the 30 mg BID group showed a 21.8% increase in the number of patients with "normal" levels of ALT compared to the placebo group. At week 16, these patients showed a 16.5% increase in the number of patients with "normal" levels of ALT compared to the placebo group. At week 24, these patients showed a 36.2% increase in the number of patients with "normal" levels of ALT compared to the placebo group. See Table 1.

TABLE 1

Summary of Percent Change of Alanine Aminotransferase During Apremilast Treatment (PALACE 1, 2, and 3)

| | | Normal | | | | |
|---|---|---|---|---|---|---|
| | Baseline High | | | % difference from | High | |
| ALT | n | n | % | Placebo | n | % |
| Week Placebo | 70 | 26 | 37.1% | 0 | 44 | 62.9% |
| 4    20 mg BID | 83 | 38 | 45.8% | 8.7 | 45 | 54.2% |
|      30 mg BID | 56 | 33 | 58.9% | 21.8 | 23 | 41.1% |
| Week Placebo | 65 | 33 | 50.8% | 0 | 32 | 49.2% |
| 16   20 mg BID | 76 | 48 | 63.2% | 12.4 | 28 | 36.8% |
|      30 mg BID | 52 | 35 | 67.3% | 16.5 | 17 | 32.7% |
| Week Placebo | 15 | 6 | 40.0% | 0 | 9 | 60.0% |
| 24   20 mg BID | 51 | 28 | 54.9% | 14.9 | 23 | 45.1% |
|      30 mg BID | 42 | 32 | 76.2% | 36.2 | 10 | 23.8% |

Of the subjects tested for AST at week 4, the 20 mg BID group showed a 9% increase in the number of patients with "normal" levels of AST compared to the placebo group. At week 16, these patients showed a 4.3% decrease in the number of patients with "normal" levels of AST compared to the placebo group. At week 24, these patients showed a 5.6% increase in the number of patients with "normal" levels of AST compared to the placebo group. See Table 2.

Of the subjects tested for AST at week 4, the 30 mg BID group showed a 5.4% increase in the number of patients with "normal" levels of AST compared to the placebo group. At week 16, these patients showed a 9.2% increase in the number of patients with "normal" levels of AST compared to the placebo group. At week 24, these patients showed a 25.8% increase in the number of patients with "normal" levels of AST compared to the placebo group. See Table 2.

TABLE 2

Summary of Percent Change of Aspartate Aminotransferase During Apremilast Treatment (PALACE 1, 2, and 3)

| | | Normal | | | | |
|---|---|---|---|---|---|---|
| | Baseline High | | | % difference from | High | |
| AST | n | n | % | Placebo | n | % |
| Week Placebo | 42 | 22 | 52.4% | 0 | 20 | 47.6% |
| 4    20 mg BID | 44 | 27 | 61.4% | 9 | 17 | 38.6% |
|      30 mg BID | 45 | 26 | 57.8% | 5.4 | 19 | 42.2% |
| Week Placebo | 38 | 25 | 65.8% | 0 | 13 | 34.2% |
| 16   20 mg BID | 39 | 24 | 61.5% | −4.3 | 15 | 38.5% |
|      30 mg BID | 40 | 30 | 75.0% | 9.2 | 10 | 25.0% |
| Week Placebo | 14 | 7 | 50.0% | 0 | 7 | 50.0% |
| 24   20 mg BID | 27 | 15 | 55.6% | 5.6 | 12 | 44.4% |
|      30 mg BID | 33 | 25 | 75.8% | 25.8 | 8 | 24.2% |

TABLE 3

Levels of Alanine Aminotransferase at Week 24 of Apremilast Treatment in Placebo Group (PALACE 1, 2, and 3)

| | Placebo Week 24 ALT | | | | | | | |
|---|---|---|---|---|---|---|---|---|
| | Low | | Normal | | High | | Total | |
| Baseline | n | % | n | % | n | % | N | % |
| Low | 0 | 0.0% | 0 | 0.0% | 0 | 0.0% | 0 | 0.0% |
| Normal | 0 | 0.0% | 129 | 92.8% | 10 | 7.2% | 139 | 93.3% |
| High | 0 | 0.0% | 3 | 30.0% | 7 | 70.0% | 10 | 6.7% |
| Total | 0 | 0.0% | 132 | 88.6% | 17 | 11.4% | 149 | 100.0% |

TABLE 4

Levels of Alanine Aminotransferase at Week 24 of Apremilast Treatment in 20 mg BID Group (PALACE 1, 2, and 3)

| | APR 20 mg BID Week 24 ALT | | | | | | | |
|---|---|---|---|---|---|---|---|---|
| | Low | | Normal | | High | | Total | |
| Baseline | n | % | n | % | n | % | N | % |
| Low | 0 | 0.0% | 0 | 0.0% | 0 | 0.0% | 0 | 0.0% |
| Normal | 0 | 0.0% | 365 | 95.5% | 17 | 4.5% | 382 | 89.0% |
| High | 0 | 0.0% | 26 | 55.3% | 21 | 44.7% | 47 | 11.0% |
| Total | 0 | 0.0% | 391 | 91.1% | 38 | 8.9% | 429 | 100.0% |

TABLE 5

Levels of Alanine Aminotransferase at Week 24 of Apremilast Treatment in 30 mg BID Group (PALACE 1, 2, and 3)

| | APR 30 mg BID Week 24 ALT | | | | | | | |
|---|---|---|---|---|---|---|---|---|
| | Low | | Normal | | High | | Total | |
| Baseline | n | % | n | % | n | % | N | % |
| Low | 0 | 0.0% | 0 | 0.0% | 0 | 0.0% | 0 | 0.0% |
| Normal | 0 | 0.0% | 370 | 95.6% | 17 | 4.4% | 387 | 90.8% |
| High | 0 | 0.0% | 29 | 74.4% | 10 | 25.6% | 39 | 9.2% |
| Total | 0 | 0.0% | 399 | 93.7% | 27 | 6.3% | 426 | 100.0% |

TABLE 6

Levels of Aspartate Aminotransferase at Week 24 of Apremilast Treatment in Placebo Group (PALACE 1, 2, and 3)

| | Placebo Week 24 AST | | | | | | | |
|---|---|---|---|---|---|---|---|---|
| | Low | | Normal | | High | | Total | |
| Baseline | n | % | n | % | n | % | N | % |
| Low | 0 | 0.0% | 0 | 0.0% | 0 | 0.0% | 0 | 0.0% |
| Normal | 0 | 0.0% | 123 | 89.8% | 14 | 10.2% | 137 | 93.2% |
| High | 0 | 0.0% | 6 | 60.0% | 4 | 40.0% | 10 | 6.8% |
| Total | 0 | 0.0% | 129 | 87.8% | 18 | 12.2% | 147 | 100.0% |

TABLE 7

Levels of Aspartate Aminotransferase at Week 24 of Apremilast Treatment in 20 mg BID Group (PALACE 1, 2, and 3)

| | APR 20 mg BID Week 24 AST | | | | | | | |
|---|---|---|---|---|---|---|---|---|
| | Low | | Normal | | High | | Total | |
| Baseline | n | % | n | % | n | % | N | % |
| Low | 0 | 0.0% | 0 | 0.0% | 0 | 0.0% | 0 | 0.0% |
| Normal | 0 | 0.0% | 383 | 95.0% | 20 | 5.0% | 403 | 94.6% |
| High | 0 | 0.0% | 14 | 60.9% | 9 | 39.1% | 23 | 5.4% |
| Total | 0 | 0.0% | 397 | 93.2% | 29 | 6.8% | 426 | 100.0% |

TABLE 8

Levels of Aspartate Aminotransferase at Week 24 of Apremilast Treatment in 30 mg BID Group (PALACE 1, 2, and 3)

| | APR 30 mg BID Week 24 AST | | | | | | | |
|---|---|---|---|---|---|---|---|---|
| | Low | | Normal | | High | | Total | |
| Baseline | n | % | n | % | n | % | N | % |
| Low | 0 | 0.0% | 0 | 0.0% | 0 | 0.0% | 0 | 0.0% |
| Normal | 0 | 0.0% | 379 | 96.2% | 15 | 3.8% | 394 | 92.9% |
| High | 0 | 0.0% | 22 | 73.3% | 8 | 26.7% | 30 | 7.1% |
| Total | 0 | 0.0% | 401 | 94.6% | 23 | 5.4% | 424 | 100.0% |

TABLE 9

Percent of Patients With Changed Alanine Aminotransferase Levels at End of Apremilast Treatment, by Treatment Group (PALACE 1, 2, and 3) ALT

| Treatment | High to Normal | Normal to High | Net Benefit |
|---|---|---|---|
| Placebo | 30.0% | 7.2% | 15.0% |
| APR 20 BID | 55.3% | 4.5% | 40.6% |
| APR 30 BID | 74.4% | 4.4% | 51.8% |
| Difference between Placebo and APR 30 BID | 44.4% | -2.8% | 36.8% |

TABLE 10

Percent of Patients With Changed Aspartate Aminotransferase Levels at End of Apremilast Treatment, by Treatment Group (PALACE 1, 2, and 3) AST

| Treatment | High to Normal | Normal to High | Net Benefit |
|---|---|---|---|
| Placebo | 60.0% | 10.2% | 25.0% |
| APR 20 BID | 60.9% | 5.0% | 32.6% |
| APR 30 BID | 73.3% | 3.8% | 48.9% |
| Difference between Placebo and APR 30 BID | 13.3% | -6.4% | 23.9% |

5.3 Clinical Data of Treating or Managing a Liver Disease or a Liver Function Abnormality Using Apremilast (PSOR-008 and PSOR-009)

Apremilast was studied in Phase 3 trials in patients with moderate to severe plaque psoriasis. Patients in these studies showed improvement in liver functions as well as a reduction of liver function test (LFT) abnormalities. The improvement in mild baseline liver function test abnormalities has been observed with apremilast daily use without any prescribed changes in physical activity, social or dietary habits. During the course of the study, there was observed a higher proportion of subjects in the apremilast treatment group (30 mg BID) with normal LFTs (i.e. normal levels of ALT and AST) at subsequent placebo-controlled study visits at week 16. See Tables 11 to 16 from PSOR-008 and PSOR-009 studies.

Of the subjects tested for ALT at week 16, the 30 mg BID group showed a 3.1% increase in the number of patients who went from high to normal levels of ALT compared to the placebo group. See Table 15.

Of the subjects tested for AST at week 16, the 30 mg BID group showed a 17.9% increase in the number of patients who went from high to normal levels of AST compared to the placebo group. See Table 16.

TABLE 11

Levels of Alanine Aminotransferase at Week 16 of Apremilast Treatment in Placebo Group (PSOR-008 and PSOR-009)

| | Placebo Week 16 ALT | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 305 | 94.1% | 19 | 5.9% | 324 | 89.8% |
| High | 0 | 0.0% | 20 | 54.1% | 17 | 45.9% | 37 | 10.2% |
| Total | 0 | 0.0% | 325 | 90.0% | 36 | 10.0% | 361 | 100.0% |

TABLE 12

Levels of Alanine Aminotransferase at Week 16 of Apremilast Treatment in 30 mg BID Group (PSOR-008 and PSOR-009)

| | APR 30 mg BID Week 16 ALT | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 646 | 96.3% | 25 | 3.7% | 671 | 89.7% |
| High | 0 | 0.0% | 44 | 57.1% | 33 | 42.9% | 77 | 10.3% |
| Total | 0 | 0.0% | 690 | 92.2% | 58 | 7.8% | 748 | 100.0% |

TABLE 13

Levels of Aspartate Aminotransferase at Week 16 of Apremilast Treatment in Placebo Group (PSOR-008 and PSOR-009)

| | Placebo Week 16 AST | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 320 | 97.6% | 8 | 2.4% | 328 | 90.9% |
| High | 0 | 0.0% | 14 | 42.4% | 19 | 57.6% | 33 | 9.1% |
| Total | 0 | 0.0% | 334 | 92.5% | 27 | 7.5% | 361 | 100.0% |

TABLE 14

Levels of Aspartate Aminotransferase at Week 16 of Apremilast Treatment in 30 mg BID Group (PSOR-008 and PSOR-009)

| | APR 30 mg BID Week 16 AST | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 666 | 97.2% | 19 | 2.8% | 685 | 91.6% |
| High | 0 | 0.0% | 38 | 60.3% | 25 | 39.7% | 63 | 8.4% |
| Total | 0 | 0.0% | 704 | 94.1% | 44 | 5.9% | 748 | 100.0% |

TABLE 15

Percent of Patients With Changed Alanine Aminotransferase Levels at End of Apremilast Treatment, by Treatment Group (PSOR-008 and PSOR-009) ALT

| Treatment | High to Normal | Normal to High | Net Benefit |
|---|---|---|---|
| Placebo | 54.1% | 5.9% | 35.7% |
| APR 30 BID | 57.1% | 3.7% | 53.7% |
| Difference | 3.1% | −2.1% | 17.9% |

TABLE 16

Percent of Patients With Changed Aspartate Aminotransferase Levels at End of Apremilast Treatment, by Treatment Group (PSOR-008 and PSOR-009) AST

| Treatment | High to Normal | Normal to High | Net Benefit |
|---|---|---|---|
| Placebo | 42.4% | 2.4% | 34.1% |
| APR 30 BID | 60.3% | 2.8% | 46.3% |
| Difference | 17.9% | 0.3% | 12.2% |

5.4 Clinical Data of Treating or Managing a Liver Disease or a Liver Function Abnormality Using Apremilast (RA-002)

Apremilast was studied in a Phase 2 trial in patients with active rheumatoid arthritis who have had an inadequate response to methotrexate. Patients in these studies showed improvement in liver functions as well as a reduction of liver function test (LFT) abnormalities. The improvement in mild baseline liver function test abnormalities has been observed with apremilast daily use without any prescribed changes in physical activity, social or dietary habits. During the course of the study, there was observed a higher proportion of subjects in the 30 mg BID apremilast treatment group with normal LFTs at subsequent placebo-controlled study visits at week 16. See Tables 17 to 24 from RA-002 studies.

Of the subjects tested for ALT at week 16, the 30 mg BID group showed a 0% increase in the number of patients who went from high to normal levels of ALT compared to the placebo group. See Table 23.

Of the subjects tested for AST at week 16, the 30 mg BID group showed a 50% increase in the number of patients who went from high to normal levels of AST compared to the placebo group. See Table 24.

TABLE 17

Levels of Alanine Aminotransferase at Week 16 of Apremilast Treatment in Placebo Group (RA-002)

| | Placebo Week 16 ALT | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 65 | 100.0% | 0 | 0.0% | 65 | 91.5% |
| High | 0 | 0.0% | 4 | 66.7% | 2 | 33.3% | 6 | 8.5% |

TABLE 17-continued

Levels of Alanine Aminotransferase at Week 16 of Apremilast Treatment in Placebo Group (RA-002)

Placebo
Week 16
ALT

| | Low | | Normal | | High | | Total | |
|---|---|---|---|---|---|---|---|---|
| Baseline | n | % | n | % | n | % | n | % |
| Total | 0 | 0.0% | 69 | 97.2% | 2 | 2.8% | 71 | 100.0% |

TABLE 18

Levels of Alanine Aminotransferase at Week 16 of Apremilast Treatment in 20 mg BID Group (RA-002)

APR 20 mg BID
Week 16
ALT

| | Low | | Normal | | High | | Total | |
|---|---|---|---|---|---|---|---|---|
| Baseline | n | % | n | % | n | % | n | % |
| Low | 0 | 0.0% | 0 | 0.0% | 0 | 0.0% | 0 | 0.0% |
| Normal | 0 | 0.0% | 63 | 95.5% | 3 | 4.5% | 66 | 94.3% |
| High | 0 | 0.0% | 1 | 25.0% | 3 | 75.0% | 4 | 5.7% |
| Total | 0 | 0.0% | 64 | 91.4% | 6 | 8.6% | 70 | 100.0% |

TABLE 19

Levels of Alanine Aminotransferase at Week 16 of Apremilast Treatment in 30 mg BID Group (RA-002)

APR 30 mg BID
Week 16
ALT

| | Low | | Normal | | High | | Total | |
|---|---|---|---|---|---|---|---|---|
| Baseline | n | % | n | % | n | % | n | % |
| Low | 0 | 0.0% | 0 | 0.0% | 0 | 0.0% | 0 | 0.0% |
| Normal | 0 | 0.0% | 62 | 96.9% | 2 | 3.1% | 64 | 95.5% |
| High | 0 | 0.0% | 2 | 66.7% | 1 | 33.3% | 3 | 4.5% |
| Total | 0 | 0.0% | 64 | 95.5% | 3 | 4.5% | 67 | 100.0% |

TABLE 20

Levels of Aspartate Aminotransferase at Week 16 of Apremilast Treatment in Placebo Group (RA-002)

Placebo
Week 16
AST

| | Low | | Normal | | High | | Total | |
|---|---|---|---|---|---|---|---|---|
| Baseline | n | % | n | % | n | % | n | % |
| Low | 0 | 0.0% | 0 | 0.0% | 0 | 0.0% | 0 | 0.0% |
| Normal | 0 | 0.0% | 65 | 97.0% | 2 | 3.0% | 67 | 94.4% |
| High | 0 | 0.0% | 2 | 50.0% | 2 | 50.0% | 4 | 5.6% |
| Total | 0 | 0.0% | 67 | 94.4% | 4 | 5.6% | 71 | 100.0% |

TABLE 21

Levels of Aspartate Aminotransferase at Week 16 of Apremilast Treatment in 20 mg BID Group (RA-002)

APR 20 mg BID
Week 16
AST

| | Low | | Normal | | High | | Total | |
|---|---|---|---|---|---|---|---|---|
| Baseline | n | % | n | % | n | % | n | % |
| Low | 0 | 0.0% | 0 | 0.0% | 0 | 0.0% | 0 | 0.0% |
| Normal | 0 | 0.0% | 64 | 97.0% | 2 | 3.0% | 66 | 94.3% |
| High | 0 | 0.0% | 2 | 50.0% | 2 | 50.0% | 4 | 5.7% |
| Total | 0 | 0.0% | 66 | 94.3% | 4 | 5.7% | 70 | 100.0% |

TABLE 22

Levels of Aspartate Aminotransferase at Week 16 of Apremilast Treatment in 30 mg BID Group (RA-002)

APR 30 mg BID
Week 16
AST

| | Low | | Normal | | High | | Total | |
|---|---|---|---|---|---|---|---|---|
| Baseline | n | % | n | % | n | % | n | % |
| Low | 0 | 0.0% | 0 | 0.0% | 0 | 0.0% | 0 | 0.0% |
| Normal | 0 | 0.0% | 61 | 95.3% | 3 | 4.7% | 64 | 95.5% |
| High | 0 | 0.0% | 3 | 100.0% | 0 | 0.0% | 3 | 4.5% |
| Total | 0 | 0.0% | 64 | 95.5% | 3 | 4.5% | 67 | 100.0% |

TABLE 23

Percent of Patients With Changed Alanine Aminotransferase Levels at End of Apremilast Treatment, by Treatment Group (RA-002)
ALT

| Treatment | High to Normal | Normal to High | Net Benefit |
|---|---|---|---|
| Placebo | 66.7% | 0.0% | 66.7% |
| APR 20 BID | 25.0% | 4.5% | 14.3% |
| APR 30 BID | 66.7% | 3.1% | 40.0% |
| Difference between Placebo and APR 30 BID | 0.0% | 3.1% | −26.7% |

TABLE 24

Percent of Patients With Changed Aspartate Aminotransferase Levels at End of Apremilast Treatment, by Treatment Group (RA-002)
AST

| Treatment | High to Normal | Normal to High | Net Benefit |
|---|---|---|---|
| Placebo | 50.0% | 3.0% | 33.3% |
| APR 20 BID | 50.0% | 3.0% | 33.3% |
| APR 30 BID | 100.0% | 4.7% | 50.0% |
| Difference between Placebo and APR 30 BID | 50.0% | 1.7% | 16.7% |

5.5 Clinical Data of Treating or Managing a Liver Disease or a Liver Function Abnormality Using Apremilast (PSA-005)

Apremilast was studied in a Phase 3 trial in patients with active psoriatic arthritis who have not been previously treated with disease-modifying antirheumatic drugs. Patients in these studies showed improvement in liver functions as well as a reduction of liver function test (LFT) abnormalities. The improvement in mild baseline liver function test abnormalities has been observed with apremilast daily use without any prescribed changes in physical activity, social or dietary habits. During the course of the study, there was observed a higher proportion of subjects in both the 20 mg and 30 mg BID apremilast treatment groups with normal LFTs (i.e. normal levels of ALT and AST) at subsequent placebo-controlled study visits at week 24. See Tables 25 to 34 from PSA-005 studies.

Of the subjects tested for ALT at week 24, the 30 mg BID group showed a 22.7% increase in the number of patients who went from high to normal levels of ALT compared to the placebo group. See Table 33.

Of the subjects tested for AST at week 24, the 30 mg BID group showed a 25% increase in the number of patients who went from high to normal levels of AST compared to the placebo group. See Table 34.

TABLE 25

Percent of Patients With Changed Alanine Aminotransferase Levels at Various Weeks of Apremilast Treatment, by Treatment Group (PSA-005)

| | ALT | Baseline High n | Normal n | Normal % | High n | High % |
|---|---|---|---|---|---|---|
| Week 4 | Placebo | 11 | 6 | 54.5% | 5 | 45.5% |
| | 20 mg BID | 10 | 7 | 70.0% | 3 | 30.0% |
| | 30 mg BID | 11 | 3 | 27.3% | 8 | 72.7% |
| Week 16 | Placebo | 9 | 5 | 55.6% | 4 | 44.4% |
| | 20 mg BID | 8 | 7 | 87.5% | 1 | 12.5% |
| | 30 mg BID | 11 | 7 | 63.6% | 4 | 36.4% |
| Week 24 | Placebo | 2 | 1 | 50.0% | 1 | 50.0% |
| | 20 mg BID | 8 | 7 | 87.5% | 1 | 12.5% |
| | 30 mg BID | 11 | 8 | 72.7% | 3 | 27.3% |

TABLE 26

Percent of Patients With Changed Aspartate Aminotransferase Levels at Various Weeks of Apremilast Treatment, by Treatment Group (PSA-005)

| | AST | Baseline High n | Normal n | Normal % | High n | High % |
|---|---|---|---|---|---|---|
| Week 4 | Placebo | 12 | 7 | 58.3% | 5 | 41.7% |
| | 20 mg BID | 7 | 2 | 28.6% | 5 | 71.4% |
| | 30 mg BID | 12 | 6 | 50.0% | 6 | 50.0% |
| Week 16 | Placebo | 10 | 6 | 60.0% | 4 | 40.0% |
| | 20 mg BID | 5 | 4 | 80.0% | 1 | 20.0% |
| | 30 mg BID | 12 | 7 | 58.3% | 5 | 41.7% |
| Week 24 | Placebo | 2 | 1 | 50.0% | 1 | 50.0% |
| | 20 mg BID | 5 | 3 | 60.0% | 2 | 40.0% |
| | 30 mg BID | 12 | 9 | 75.0% | 3 | 25.0% |

TABLE 27

Levels of Alanine Aminotransferase at Week 24 of Apremilast Treatment in Placebo Group (PSA-005)

| | Placebo Week 24 ALT | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 48 | 94.1% | 3 | 5.9% | 51 | 96.2% |
| High | 0 | 0.0% | 1 | 50.0% | 1 | 50.0% | 2 | 3.8% |
| Total | 0 | 0.0% | 49 | 92.5% | 4 | 7.5% | 53 | 100.0% |

TABLE 28

Levels of Alanine Aminotransferase at Week 24 of Apremilast Treatment in 20 mg BID Group (PSA-005)

| | APR 20 mg BID Week 24 ALT | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 145 | 96.7% | 5 | 3.3% | 150 | 94.9% |
| High | 0 | 0.0% | 7 | 87.5% | 1 | 12.5% | 8 | 5.1% |
| Total | 0 | 0.0% | 152 | 96.2% | 6 | 3.8% | 158 | 100.0% |

TABLE 29

Levels of Alanine Aminotransferase at Week 24 of Apremilast Treatment in 30 mg BID Group (PSA-005)

| | APR 30 mg BID Week 24 ALT | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 136 | 95.1% | 7 | 4.9% | 143 | 92.9% |
| High | 0 | 0.0% | 8 | 72.7% | 3 | 27.3% | 11 | 7.1% |
| Total | 0 | 0.0% | 144 | 93.5% | 10 | 6.5% | 154 | 100.0% |

TABLE 30

Levels of Aspartate Aminotransferase at Week 24 of Apremilast Treatment in Placebo Group (PSA-005)

| | Placebo Week 24 AST | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 49 | 96.1% | 2 | 3.9% | 51 | 96.2% |
| High | 0 | 0.0% | 1 | 50.0% | 1 | 50.0% | 2 | 3.8% |
| Total | 0 | 0.0% | 50 | 94.3% | 3 | 5.7% | 53 | 100.0% |

TABLE 31

Levels of Aspartate Aminotransferase at Week 24 of Apremilast Treatment in 20 mg BID Group (PSA-005)

| | APR 20 mg BID Week 24 AST | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 149 | 98.0% | 3 | 2.0% | 152 | 96.8% |
| High | 0 | 0.0% | 3 | 60.0% | 2 | 40.0% | 5 | 3.2% |
| Total | 0 | 0.0% | 152 | 96.8% | 5 | 3.2% | 157 | 100.0% |

TABLE 32

Levels of Aspartate Aminotransferase at Week 24 of Apremilast Treatment in 30 mg BID Group (PSA-005)

| | APR 30 mg BID Week 24 AST | | | | | | | |
|---|---|---|---|---|---|---|---|---|
| | Low | | Normal | | High | | Total | |
| Baseline | n | % | n | % | n | % | n | % |
| Low | 0 | 0.0% | 0 | 0.0% | 0 | 0.0% | 0 | 0.0% |
| Normal | 0 | 0.0% | 138 | 97.9% | 3 | 2.1% | 141 | 92.2% |
| High | 0 | 0.0% | 9 | 75.0% | 3 | 25.0% | 12 | 7.8% |
| Total | 0 | 0.0% | 147 | 96.1% | 6 | 3.9% | 153 | 100.0% |

TABLE 33

Percent of Patients With Changed Alanine Aminotransferase Levels at End of Apremilast Treatment, by Treatment Group (PSA-005) ALT

| Treatment | High to Normal | Normal to High | Net Benefit |
|---|---|---|---|
| Placebo | 50.0% | 5.9% | 20.0% |
| APR 20 BID | 87.5% | 3.3% | 53.8% |
| APR 30 BID | 72.7% | 4.9% | 44.4% |
| Difference between Placebo and APR 30 BID | 22.7% | −1.0% | 24.4% |

TABLE 34

Percent of Patients With Changed Aspartate Aminotransferase Levels at End of Apremilast Treatment, by Treatment Group (PSA-005) AST

| Treatment | High to Normal | Normal to High | Net Benefit |
|---|---|---|---|
| Placebo | 50.0% | 3.9% | 25.0% |
| APR 20 BID | 60.0% | 2.0% | 37.5% |
| APR 30 BID | 75.0% | 2.1% | 60.0% |
| Difference between Placebo and APR 30 BID | 25.0% | −1.8% | 35.0% |

5.6 Clinical Data of Treating or Managing Pruritus Using Apremilast (ESTEEM 1 and 2)

Two randomized, double-blind, placebo controlled, multicenter clinical studies were performed in patients with moderate to severe plaque psoriasis who had a body surface area (BSA) involvement of ≥10%, static Physician Global Assessment (sPGA) of ≥3 (moderate or severe disease), Psoriasis Area and Severity Index (PASI) score ≥12, and who were candidates for phototherapy or systemic therapy. Patients were randomized with Apremilast in an amount of 30 mg twice per day or placebo for the first 16 weeks, and from Weeks 16 to 32, all patients received Apremilast in an amount of 30 mg twice per day.

Results:

Significant improvements (reductions) in pruritus, as measured by the mean change in area from Baseline, were detected in patients receiving Apremilast compared with placebo-treated patients at Week 16 (ESTEEM 1: Apremilast 30 mg BID: −31.5%; placebo: −7.5%; and ESTEEM 2: Apremilast 30 mg BID: −33.5%; placebo: −12.2%). See Table 35.

TABLE 35

| Clinical response at Week 16 in Studies ESTEEM 1 AND 2 | | | | |
|---|---|---|---|---|
| | ESTEEM 1 | | ESTEEM 2 | |
| | Placebo | Apremilast 30 mg BID | Placebo | Apremilast 30 mg BID |
| Change in Pruritus Visual Analog Scale (mm ± SD) | −7.3 (±27.08) | −31.5 (±32.43) | −12.2 (±30.94) | −33.5 (±35.46) |

Apremilast appears to demonstrate a dose response with greater improvement of abnormal LFTs for the 30 mg BID compared to the apremilast 20 mg BID treatment groups, and a progressively higher proportion of subjects with abnormal LFTs having normal LFTs with longer periods of treatment. The proportion of subjects with normal LFTs increases with treatment in the apremilast treatment groups from baseline to week 4 to week 16 and further improvement by week 24. The above data indicate that apremilast treatment improves liver function.

All of the references cited herein are incorporated by reference in their entirety. While the methods provided herein have been described with respect to the particular embodiments, it will be apparent to those skilled in the art that various changes and modifications can be made without departing from the spirit and scope as recited by the appended claims.

The embodiments described above are intended to be merely exemplary and those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method of treating or managing a patient having fatty liver disease; hepatic fibrosis; hemochromatosis; acute porphyria; sclerosis cholangitis; cholestatic jaundice; primary biliary cirrhosis; Wilson's disease; or hepatic steatosis, wherein the method comprises orally administering to the patient an effective amount of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug or salt thereof.

2. The method of claim 1, wherein the stereomerically pure (+)-2-[1-(3-ethoxy-4-methoxyphenyl)-2-methylsulfonylethyl]-4-acetylaminoisoindoline-1,3-dione is administered once or twice daily.

3. The method of claim 2, wherein the stereomerically pure (+)-2-[1-(3-ethoxy-4-methoxyphenyl)-2-methylsulfonylethyl]-4-acetylaminoisoindoline-1,3-dione is administered in an amount of about 10 mg, about 20 mg, about 30 mg, or about 40 mg, once daily.

4. The method of claim 2, wherein the stereomerically pure (+)-2-[1-(3-ethoxy-4-methoxyphenyl)-2-methylsulfonylethyl]-4-acetylaminoisoindoline-1,3-dione is administered in an amount of about 10 mg, about 20 mg, about 30 mg, or about 40 mg, twice daily.

5. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 90% by weight of (+) isomer based on the total weight percent of the compound.

6. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 95% by weight of (+) isomer based on the total weight percent of the compound.

7. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 96% by weight of (+) isomer based on the total weight percent of the compound.

8. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 97% by weight of (+) isomer based on the total weight percent of the compound.

9. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 98% by weight of (+) isomer based on the total weight percent of the compound.

10. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 99% by weight of (+) isomer based on the total weight percent of the compound.

11. The method of claim 1, wherein the stereomerically pure (+)-2-[1-(3-ethoxy-4-methoxyphenyl)-2-methylsulfonylethyl]-4-acetylaminoisoindoline-1,3-dione is administered in a tablet form.

12. The method of claim 11, wherein the tablet comprises a 10 mg, 20 mg, 30 mg, or 40 mg dose of stereomerically pure (+)-2-[1-(3-ethoxy-4-methoxyphenyl)-2-methyl sulfonylethyl]-4-acetylaminoisoindoline-1,3-dione.

13. The method of claim 12, wherein the tablet comprises a 10 mg dose of stereomerically pure (+)-2-[1-(3-ethoxy-4-methoxyphenyl)-2-methylsulfonylethyl]-4-acetylaminoisoindoline-1,3-dione.

14. The method of claim 12, wherein the tablet comprises a 20 mg dose of stereomerically pure (+)-2-[1-(3-ethoxy-4-methoxyphenyl)-2-methylsulfonylethyl]-4-acetylaminoisoindoline-1,3-dione.

15. The method of claim 12, wherein the tablet comprises a 30 mg dose of stereomerically pure (+)-2-[1-(3-ethoxy-4-methoxyphenyl)-2-methylsulfonylethyl]-4-acetylaminoisoindoline-1,3-dione.

16. The method of claim 12, wherein the tablet comprises a 40 mg dose of stereomerically pure (+)-2-[1-(3-ethoxy-4-methoxyphenyl)-2-methylsulfonylethyl]-4-acetylaminoisoindoline-1,3-dione.

17. The method of claim 12, wherein the tablet further comprises lactose monohydrate, microcrystalline cellulose, croscarmellose sodium, magnesium stearate, polyvinyl alcohol, titanium dioxide, polyethylene glycol, and talc.

18. The method of claim 17, wherein the tablet further comprises iron oxide red.

19. The method of claim 17, wherein the tablet further comprises iron oxide red and iron oxide yellow.

20. The method of claim 17, wherein the tablet further comprises iron oxide red, iron oxide yellow, and iron oxide black.

21. The method of claim 1, wherein the method further comprises administering to the patient a therapeutically effective amount of one or more second active agents.

22. The method of claim 21, wherein the one or more second active agents are medications for treating a liver disease or liver function abnormality.

23. The method of claim 1, wherein the liver disease is relapsed or refractory to a prior treatment.

24. The method of claim 1, wherein the fatty liver disease is nonalcoholic fatty liver disease.

25. The method of claim 1, wherein the fatty liver disease is alcoholic fatty liver disease.

26. The method of claim 24, wherein the nonalcoholic fatty liver disease is pediatric nonalcoholic fatty liver disease.

27. The method of claim 1, wherein the liver function abnormality comprises an elevated level of alanine aminotransferase or aspartate aminotransferase in the patient.

28. The method of claim 1, wherein the method comprises administering stereomerically pure (+)-2-[1-(3-ethoxy-4-methoxyphenyl)-2-methylsulfonylethyl]-4-acetylaminoisoindoline-1,3-dione, substantially free of any salt, solvate, or prodrug forms of (+)-2-[1-(3-ethoxy-4-methoxyphenyl)-2-methylsulfonylethyl]-4-acetylaminoisoindoline-1,3-dione.

29. The method of claim 1, wherein the method comprises administering a pharmaceutically acceptable salt of stereomerically pure (+)-2-[1-(3-ethoxy-4-methoxyphenyl)-2-methyl sulfonylethyl]-4-acetylaminoisoindoline-1,3-dione.

30. The method of claim 1, wherein the method decreases the level of alanine aminotransferase or aspartate aminotransferase in the patient.

31. The method of claim 1, wherein the method further comprises administering to the patient an additional treatment.

32. The method of claim 31, wherein the additional treatment is surgical correction.

33. The method of claim 31, wherein the additional treatment is a liver transplant.

34. A method of treating or managing pruritus associated with a liver disease or a liver function abnormality, wherein the method comprises orally administering to a patient having a liver disease or a liver function abnormality an effective amount of the compound, wherein the compound is stereomerically pure (+)-2-[1-(3-ethoxy-4-methoxyphenyl)-2-methylsulfonylethyl]-4-acetylaminoisoindoline-1,3-dione, or a pharmaceutically acceptable prodrug or salt thereof.

* * * * *